US008114396B2

(12) United States Patent
Horn et al.

(10) Patent No.: US 8,114,396 B2
(45) Date of Patent: \*Feb. 14, 2012

(54) MEGASPHAERA ELSDENII STRAIN AND ITS USES

(75) Inventors: Charles Henry Horn, Pretoria (ZA); Albrecht Kistner, Pretoria (ZA); Barend Jacobus Greyling, Pretoria (ZA); Alexandra Helena Smith, Douglasdale (ZA)

(73) Assignees: Agricultural Research Council, Pretoria (ZA); MS Biotech, Inc., Littleton, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/325,250

(22) Filed: Nov. 30, 2008

(65) Prior Publication Data

US 2009/0246177 A1 Oct. 1, 2009

Related U.S. Application Data

(63) Continuation of application No. 10/521,847, filed as application No. PCT/ZA03/00093 on Jul. 15, 2003, now Pat. No. 7,550,139.

(30) Foreign Application Priority Data

Jul. 18, 2002 (ZA) ...................................... 02/5742

(51) Int. Cl.
*A01N 63/00* (2006.01)
(52) U.S. Cl. ........................... 424/93.4; 426/53; 435/243
(58) Field of Classification Search ........................ None
See application file for complete search history.

(56) References Cited

U.S. PATENT DOCUMENTS

| 4,138,498 | A | | 2/1979 | Das | |
| 5,380,525 | A | * | 1/1995 | Leedle et al. | ................. 424/93.4 |
| 7,550,139 | B2 | * | 6/2009 | Horn et al. | ................... 424/93.4 |

FOREIGN PATENT DOCUMENTS

WO WO 91/13146 A1 9/1991

OTHER PUBLICATIONS

Kim et al., Journal of Applied Microbiology, 2002, vol. 92, p. 976-982.*
Ouwerkerk et al., Journal of applied Microbiology, 2002, vol. 92, p. 753-758.*
Allison, M.J., et al, *Ruminal changes after overfeeding with wheat and the effect of intraruminal inoculation on adaptation to a ration containing wheat*, J. Anim Sci,, 23:1164-1170 (1964).
Braun, U., et al., *Ruminal lactic acidosis in sheep and goats*. The Veterinary Record, 130:343-349 (1992).
Dawson, KA, et al. *Digestive disorders and nutritional toxicity*, In The Rumen Microbial Ecosystem, pp. 445-459 (1988).
Kung, L., et al, *Preventing in vitro Lactate Accumulation In Ruminal Fermentations By Inoculation With Megasphaera elsdenii.*, J. Anim Sci., 73:250-256 (1995).
Lederberg, J., et al, *Replica plating and indirect selection of bacterial mutants*, J. Bact. 63:399-406 (1952).
Mackie, R.I., et al., *Microbiological and chemical changes in the rumen during the stepwise adaptation of sheep to high concentrate diets*, J. Agric Sc. Camb, 90:241-254 (1978).
Mackie, R.I., et al., *An in vivo study of ruminal micro-organisms influencing lactate turnover and its contribution to volatile fatty acid production.*, J. Agric Sc. Comb, 103:37-51 (1984).
Mackie, R.I., et al., *Changes in Lactate-Producing and Lactate-Utilizing Bacteria in Relation to pH in the rumen of Sheep During Stepwise Adaptation to a High Concentrate Diet*, Appl Environ Microbiol, 38:422-430 (1979).
Mackie, R.I., et al., *Enumeration and Isolation of Lactate-Utilizing Bacteria from the Rumen of Sheep*, Appl Environ Microbiol, 38:416-421 (1979).
Marourtek, M,, et al., *Metabolism and Some Characteristics of Ruminal Strains of Megasphaera elsenii*, Appl Environ Microbiol, 55:1570-1573 (1989).
Olumeyan, D.B., et al., *Rumen Microbial Changes in Cattle Fed Diets With or Without Salinomycin*, Appl EnvironMicrobiol, 51:340-345 (1986).
Robinson, J.A., et al., *Prevention of acute acidosis and enhancement of feed intake in the bovine by Megasphaera elsdenii*, J. Anim Sci. 70:310 (abstract) (1992).
Russell, J.B., et al., *Substrate Preferences in Rumen Bacteria: Evidence of Catabolite Regulatory Mechanisms*, Appl. Environ Microbiol, 36:319-329 (1978).
Slyter, L.L., *Influence of acidosis on rumen function*, J. Anim Sci, 43:910-929 (1976).
Therion, J.J., et al., *Effect of pH on Growth Rates of Rumen Amylolytic and Lactilytic Bacteria.*, Appl Environ Microbiol, 44:428-434 (1982).
Van Gylswyk, N.O., *Enumeration and presumptive identification of some functional groups of bacteria in the rumen of dairy cows fed grass silage-based diets*, FEMS Microbiol Ecol, 73:243-254 (1990).
Wirayawan, K.G., et al., *Probiotic control of lactate accumulation in acutely grain-fed sheep*, Aust J Agric Res, 46:1555-1568 (1995).
Donovan, J., *Subacute acidosis is costing us millions*, Hoards Dairyman, p. 666, Sep. 25 (1997).
Hutjens, M.F., *How and when feed additives may or may not pay*, Hoards Dairyman, Sep. 25 (1999).

(Continued)

*Primary Examiner* — Kade Ariani
(74) *Attorney, Agent, or Firm* — Bowditch & Dewey, LLP; Roger P. Zimmerman

(57) ABSTRACT

This invention relates to a novel strain of *Megasphaera elsdenii* and its uses. This invention further relates to preparations and methods incorporating such strain. This invention also relates to feedstuffs for ruminants and a preparation and method for the prevention and treatment of lactic acidosis in ruminants. This invention even further relates to a method of isolating a biologically pure culture of a superior ruminal microorganism in a relatively shorter time period than conventional methods. This invention yet further relates to a method of achieving any one or more of the following improvements in ruminants namely increased milk production; improved feedlot performance; improved growth rate; decrease in finishing time; lower digestive morbidity and mortality; lower incidence of lactic acidosis and related diseases; improved feed conversion efficiency; decrease in roughage content in feeds; and capability to feed on relatively higher concentrate diets.

19 Claims, 3 Drawing Sheets

OTHER PUBLICATIONS

Kelly, E.R, et al., *Lameness in Dairy Cattle and the Type of Concentrates Given*, Anim Prod 51:221 (1990).

Manson, RJ., et al., *The Influence of Concentrate Amount on Locomotion and Clinical Lameness in Dairy Cattle*, Anim Prod. 47:185-190 (1988).

Nocek, H.E., *Bovine Acidosis: Implication on Laminitis*, J. Dairy Sci, 80:1005-1028 (1997).

Brosius, J., et al., *Complete nucleotide sequence of 16S ribosomal RNA gene from Escherichia coli*, Proc. Natl. Acad. Sci, 75:4801-4805 (1978).

Dorsch, M., et al., *Some modifications in the procedure of direct sequencing of PCR amplified 16S rDNA*, J. Microbiol. Methods, 16:271-279 (1992).

Elsden, S.R, et al., *The Production of Fatty Acids by a Gram-negative Coccus*, Biochem, J., 55:183-189 (1953).

Elsden, S.R, et al., *Properties of a Fatty Acid Forming Organism isolated From The Rumen of Sheep*, J. Bacteriol. 72:681-689 (1956).

Engelmann, U., et al., *Megasphaera cerevisiae sp. Nov.: A New Gram-negative Obligately Anaerobic Coccus Isolated from Spoiled Beer*, Syst App. Microbiol., 6:287-290 (1985).

Fox, G.E., et al., *How Close is Close: 16S rRNA Sequence Identity May Not Be Sufficient To Guarantee Species Identity.*, Int J. Syst. Bacteriol., 42:166-170 (1992).

Lane, D.J., et al., *Rapid determination of 16S ribosomal RNA sequences for phylogenetic analyses*, Proc. Natl. Acad. Sci., 82:6955-6959 (1985).

Rogosa, M., *Transfer of Peptostreptococcus elsdenii*, Gutierrez et al. To a New Genus, Megasphaera [*M. elsdenii* (Gutierrez et al.) comb. Nov.], Int. J. Sys. Bacteriol., 21:187-189 (1971).

Stackebrandt, et al., *The Importance of using Outgroup Reference Organisms in Phylogenetic Studies: the Atopobium Case*, Syst. App. Microbiol, 17:39-43 (1994).

Stackebrandt, et al., *16S rRNA analyses of Sporomusa, Selenomusa and Megaphaera: on the phylogenetic Origin of Gram-positive Eubacteria*, Arch. Microbiol, 143:270-276 (1985).

Stackebrandt, et al., *Partial 16 rRNA primary structure of five Actinomyces species: phylogenetic implications and development of an Actinomyces israelii-specific oligonucleotide probe*, Journal of Gen. Microbiology, 136:37-43 (1990).

Utaker, Janne, et al., *Pylogenetic Analysis of Seven New Isolatees of Ammonia-Oxidizing Bacteria Based on 16s rRNA Gene Sequences*, System. Appl. Microbiol, 18:549.559 (1995).

Van Camp, G.Y. et al. *Structure of 16S and 23S Ribosomal RNA Genes in Campylobacter Species: Phylogenetic Analysis of the Genus Campylobaoter and Presence of Internal Transcribed Spacers*, System. Appl. Microbiol., 16:361-368 (1993).

Vandamme, et al., *Polyphasic Taxonomy, a Consensus Approach to Bacterial Systematics*, Microbiological Reviews, 60:407-438 (1996).

Woese, Carl, *Bacterial Evolution* Microbiological Reviews, 51:221-271 (1987).

Haikara, A., *The general Pectinatus and Megasphaera*, The Prokaryotes. A handbook on the Biology of Bacteria:Ecophysiology, Isolilation, Identification, Application, Second Edition, vol. II, Chapter 91, pp. 1993-2004 (1992). Barlows, A., et al., Springer-Verology, New York.

Stackbrandt, E. et al., *Partial and complete 16S rDNA sequences, their use in generation of 16S rDNA phylogenetic trees and their implications in molecular ecological studies*, Molecular Microbial Ecology Manual, 3.1.1:1-17 (1995).

Hall, M.B., *Management Strategies Against Ruminal Acidosis*, 10th Florida Ruminant Nutritional Symposium, Gainesville, Florida (Jan. 14-15, 1999).

McDaniel, B,T., et al., *Lameness in Dairy Cattle*, DHIA Awards Banquet and Annual Meeting, College of Agriculture, Univ. Arizona, Tucson (1989).

Oetzel, G.R., *Clinical aspects of Ruminal Acidosis in Dairy Cattle*, Proc. 33rd Cont. American Assoc. Bovine Practioners (Sep. 2000).

Kung, Jr., et al., "*Preventing in Vitro Lactate Accumulation in Ruminal Fermentations by Inoculation with Megasphaera elsdenii*," J. Anim. Sci., 1995,73:250-256.

\* cited by examiner

Fig. 1. Growth rates of lactate utilisers at various pH values.

Fig. 2. Growth rates (h⁻¹) of the lactate utilizing isolates, on glucose medium at various pH values.

MEGASPHAERA ELSDENII STRAIN AND ITS USES

CROSS-REFERENCE TO RELATED APPLICATIONS

This application is a continuation of U.S. application Ser. No. 10/521,847, filed Nov. 23, 2005, which is the national stage application under 35 U.S.C. 371 of International Application No. PCT/ZA2003/00092, filed Jul. 15, 2003, which claims the benefit of South African patent application No. 02/5743, filed Jul. 18, 2002. The entire contents of each of the aforementioned applications are incorporated by reference herein in their entirety.

INTRODUCTION

This invention relates to a novel strain of *Megasphaera elsdenii* and its uses. This invention further relates to preparations and methods incorporating such strain. This invention also relates to feedstuffs for ruminants and a preparation and method for the prevention and treatment of lactic acidosis in ruminants.

BACKGROUND

Lactic Acidosis

Lactic acidosis is a digestive disorder in ruminants that may occur when there is a sudden excess intake of readily fermentable carbohydrates, particularly when ruminants are switched from a diet of roughage to a high-energy or energy rich concentrate diet containing a high level of starch. The disorder is characterized by an accumulation of organic acids, especially lactic acid, in the rumen (Dawson & Allison, 1988). Studies have indicated that a gross imbalance between the numbers of lactic acid-producing bacteria and lactic acid-utilizing bacteria, brought on by a sudden increase in the proportion of readily fermentable carbohydrates in the diet is the main cause of the onset of lactic acidosis (Slyter, 1976).

Manipulating the rumen microbial population to prevent lactic acidosis by administering material containing high numbers of lactate-utilizing bacteria has been advocated for decades, but never practiced on a large scale. Manipulations to enhance lactate utilization within the rumen has been achieved by administering rumen fluid from an already adapted animal (Allison et al., 1964; Braun et al., 1992) and by administering pure or mixed bacterial cultures of lactate-utilizes (U.S. Pat. No. 1,251,483 Wilker et al., 1971; U.S. Pat. No. 3,857,971 Abdo & Chilly, 1974; U.S. Pat. No. 4,138, 498 Das, 1979; U.S. Pat. No. 5,380,525 Leedle et al., 1991; Hession & Kung, 1992; Robinson et al., 1992; Wiryawan & Brooker, 1995).

Some of these feed additives containing live bacterial cultures have been patented (U.S. Pat. No. 1,251,483 Wilker et al., 1971; U.S. Pat. No. 3,857,971 Abdo & Chilly, 1974; U.S. Pat. No. 4,138,498 Das, 1979; U.S. Pat. No. 5,380,525 Leedle et al., 1991), but not commercialized extensively or at all. In three of the patents (U.S. Pat. No. 1,251,483 Wilker et al., 1971; U.S. Pat. No. 3,857,971 Abdo & Chilly, 1974; U.S. Pat. No. 4,138,498 Das, 1979) the cultures were obtained from continuous culture fermenters with an initial inoculum of rumen fluid. However, the donor animals were not necessarily adapted to a high-concentrate diet. There is also no mention of pH tolerance for any of these cultures. In the other patent (U.S. Pat. No. 5,380,525 Leedle et al., 1991) the cultures were isolated at pH 5.3 either directly or indirectly after enrichment from ruminants adapted to high-concentrate diets.

The Incidence of Sub-acute and Acute Acidosis in Dairy Cattle

Sub-acute rumen acidosis is a common and serious health and production problem in the dairy industry because dairy cows are usually fed diets containing high levels of grains. Sub-acute and acute rumen acidosis are simply different degrees of the same problem. Acute rumen acidosis is more severe and physiological functions may be significantly impaired. The affected animal is depressed and usually ataxic, off-feed, with dilated pupils and an elevated heart rate. Diarrhoea will be obvious and the animal may become recumbent and die within 2 to 5 days after the insult (Nordlund, 1995). Acute acidosis is characterized by a dramatic reduction in ruminal pH ($\leq 5.0$), a large increase in lactic acid concentration and a large decrease in protozoa (Nocek, 1997).

Signs of sub-acute rumen acidosis are very-different from that of acute acidosis. Modern dairy management systems of group housing or group feeding make it difficult to recognize these symptoms because individual cows with these problems will usually not be noticed within a group. Herds with sub-acute rumen acidosis will present some or all of the following signs: laminitis, intermittent diarrhoea, poor appetite or cyclical feed intake, high herd cull rates for poorly defined health problems, poor body condition in spite of adequate energy intake, abscesses without obvious causes and hemoptysis (coughing of blood) or epistaxis (bleeding from the nose). Most of these signs are secondary to acidosis and most of them do not appear until weeks or months after the initial acidosis events. Contrary to feedlot cattle, dairy cows are kept for years and the management of acidosis is therefore of importance in increasing profits.

Chronic laminitis is perhaps the most consistent clinical sign of a herd with sub-acute rumen acidosis. Although the relationship between acidosis and laminitis is not completely understood, the association is widely recognized clinically and demonstrated in research trials (Kelly & Leaver, 1990; Manson & Leaver, 1988; Nocek, 1997). Furthermore, most dairy managers, veterinarians and nutritionists tend to underestimate or perhaps tolerate an abnormal incidence of laminitis and lameness in dairy herds. A survey in Minnesota demonstrated a mean incidence in lameness of 15% with a range of 0-33% (Nordlund, Garret & Oetzel, 1995). Studies in Europe have identified lameness as the third most costly health problem in dairy cows after mastitis and reproduction (McDaniel & Wilk, 1989). The management of acidosis is thus clearly of utmost importance.

A major symptom of sub-acute acidosis is decreased feed intake and decreased efficiency of milk production. Sub-acute acidosis, because of difficulties in diagnosing the problem, tends to be dismissed as other problems, such as poor management, poor forage quality e biggest economic sink to many dairy farmers because it is omni-present, particularly in high producing dairy herds.

Because of the high incidence of nutritional and metabolic disturbance amongst high producing dairy cows, nutritional strategies for improving performance with cereal based diets focus on the prevention of ruminal dysfunction by controlling acid production or by stimulating more efficient microbial growth. At present, feed additives play an important role in this regard (Hutjens, 1999). The use of yeast culture strains that specifically stimulate the growth of lactic acid utilizing bacteria generates much interest and a recent survey indicated that yeast cultures are being used in 33% of high producing Wisconsin herds. Results from various studies suggest that the Yea Sacc strain 84170 appears to be particularly well suited for altering ruminal fermentation and animal production when used in high lactate silages and feeds high in concentrates (Dawson, 1995). Production results, however, are very inconsistent. In the USA the cost for yeast culture supplementation is 4-6 cents per cow per day (Hutjens, 1999). Ionophores, because of their ability to prevent the growth of important lactic acid producers, can also play a role in managing sub-acute acidosis. Although the cost is relatively low (1-2 US cents/cow/day, Hutjens, 1999) there seems to be some resistance against the use of ionophores because of a few recent cases of ionophore toxicity. Furthermore, ionophores have not been registered in the USA for use in dairy cattle diets.

Experimentally, there have been several bacteria that have potential as direct fed microbial (DFM) for ruminants, but have not been commercialized for a number of reasons. For example, *Megasphaera elsdenii* (ME) is the major lactate-utilizing organisms in the rumen of adapted cattle fed high grain diets. When cattle are shifted from high forage to high concentrate diet, the numbers of ME are often insufficient to prevent lactic acidosis. Kung and Hessian (1995) have shown that the addition of ME B 159 prevented accumulation of lactic acid during a challenge with highly fermentable carbohydrates. Robinson et al. (1992) demonstrated that addition of a different strain of ME (407A) prevented lactic acidosis in steers.

Although the costs associated with subclinical ruminal acidosis are difficult to pinpoint, the potential costs to the dairy industry are huge (Hall, 1999). Donovan (1997) conservatively estimated the cost of subclinical acidosis to the US dairy industry at $500 million to $1 billion per year.

Elsden and Lewis (1953) first described a large, strictly anaerobic Gram-negative, fatty acid producing, non-motile coccus isolated from the rumen of sheep. However, the original isolate was lost before it had been characterized phenotypically in detail. An organism resembling the original strain was isolated from the rumen contents of sheep several years later by Elsden and his colleagues (Elsden et al., 1956). The characteristics of this organism did not fit the description of any known species at the time, but in view of the small number of isolates studied, the authors refrained from assigning the organism to a new species and genus, but referred to it as LC. Gutierrez et al. (1959) encountered a similar organism in the rumens of bloating cattle and concluded that they fell within the definition of the genus *Peptostreptococcus*, proposing the creation of a new species *P. elsdenii*. Subsequently, Rogosa (1971) demonstrated that the LC-type isolates were Gram-negative and therefore should not be included in the genus *Peptostreptococcus*. He proposed transfer of *P. elsdenii* to a new genus *Megasphaera* and the new combination *M. elsdenii*, with the isolate LC1 of Elsden et al. (1956) as the type strain. *M. elsdenii* is a strict anaerobe found mainly in the rumen of young animals and animals receiving high-concentrate diets in which lactate fermentation is particularly pronounced. The organism has also been isolated on occasion from the faeces of humans (Sugihara et al., 1974) and it ferments lactate to mainly butyrate, propionate, isobutyrate, valerat, $CO_2$, $H_2$ and sometimes trace amounts of caproate (Stewart and Bryant, 1988). Since *M. elsdenii* is not subject to catabolite repression by glucose or maltose as in *Selenomonas*, which is also a lactate utiliser occurring in the rumen, its contribution to lactate catabolism is particularly enhanced subsequent to feeding of soluble carbohydrates (Stewart and Bryant, 1988).

U.S. Pat. No. 3,956,482 (Hahn et al. 1976) discloses a method of increasing milk production in ruminants including the steps of administering to the rumen of a lactating cow acetate producing micro-organisms consisting of a mixture of 0-4% *M. elsdenii*, 30-42% *Streptococcus bovis*, 3-10% *Lactobacillus acidophilus*, 12-20% *Bifidobacterium adolescentis*, 18-44% *Bacteroides ruminicola* and 3-12% *Butyrivibrio fibrisolvens* cultured and adapted to a nutrient medium.

A major disadvantage of the invention disclosed in the above patent is the relatively high percentage (between 30-42%) of *Streptococcus bovis*, which together with *Lactobacillis* is the leading cause of lactic acidosis in ruminants. The mixture further contains a relatively low percentage of *M. elsdenii* (0-4%) and the administration of the mixture would probably aggravate or initiate ruminal lactic acidosis rather than preventing or treating it. The mixture is further exposed to atmosphere so that most of the *M. elsdenii* perish. A mixture of microorganisms is furthermore much more difficult to control than a pure culture.

U.S. Pat. No. 4,138,498 (Das, 1979) discloses a feed additive for administration to ruminants to prevent or minimize lactic acidosis when ruminants are switched from a diet of roughage to starch, comprising a bacterial culture of *M. elsdenii* admixed with an ingestible animal feed additive. *M. elsdenii* is strictly anaerobic and a disadvantage of the feed additive disclosed in this patent, over and above the disadvantages set out below, is that the *M. elsdenii* is exposed to atmosphere, leading to a rapid decline in the amount of viable cells available in the additive.

U.S. Pat. No. 5,380,525 (Leedle et al., 1991) discloses a biologically pure culture of *M. elsdenii* NRRL-18624 and its use in the facilitation of the adaptation of ruminants from a roughage or normal pasture to a high-energy starch-rich diet. The culture suffers from the disadvantages set out below.

U.S. Pat. No. 5,529,793 (Garner et al., 1996) discloses a mixture of lactic acid producing bacteria and a lactate utilizing bacteria such a *M. elsdenii* with a dry formulation or an animal feedlot diet for improving the utilization of feedstuffs by a ruminant. A disadvantage of this invention is that *M. elsdenii* is generally strictly anaerobic and the application thereof to dry feedstuffs would result in most of the cells dying.

The applicants have evaluated the above strains of *M. elsdenii* and have deducted that they are generally not suitable for commercialization and large scale preventative treatment of lactic acidosis in ruminants because of the following disadvantages of these strains namely they are not:

highly active and adapted to proliferate in the rumen of animals on high-concentrate diets;

capable of proliferating at relatively low pH values below pH 5.0 and as low as 4.5, characterized as acute acidosis;

resistant to ionophore antibiotics commonly added to feedlot diets; and capable of preferentially using lactate as a carbon source even in the presence of soluble carbohydrates such as glucose and maltose.

Further disadvantages of these strains are that, generally, they:

have a relatively low growth rate, i.e. less than 0.938 $h^{-1}$;

do not have the ability to grow on reducing sugars as well as on lactate;

have a relatively low biomass output rate, i.e. less than 0.39 g $(l.h)^{-1}$;

are not ionophore resistant; and produce predominantly propionate and butyrate and not predominantly acetate.

OBJECT OF THE INVENTION

It is therefore an object of the present invention to provide a novel strain of *M. elsdenii* and its uses, and preparations and methods incorporating such strain with which the aforesaid disadvantages can be overcome or at least minimized.

SUMMARY OF THE INVENTION

According to a first aspect of the invention there is provided a biologically pure bacterial culture of *M. elsdenii* having substantially the same 16S ribosomal RNA sequence as that of the *M. elsdenii* strain CH4 deposited on Mar. 18, 2002 at NCIMB, Aberdeen, Scotland, UK under number NCIMB 41125, the *M. elsdenii* strain CH3 deposited on Nov. 24, 2010 at NCIMB. Aberdeen. Scotland, UK under number NCIMB 41787, and the *M. elsdenii* strain CH7 deposited on Nov. 24, 2010 at NCIMB, Aberdeen, Scotland. UK under number NCIMB 41788. All restrictions imposed by the depositor on the availability of the deposited material will be irrevocably removed upon the granting of the patent.

According to a second aspect of the invention there is provided a biologically pure bacterial culture of the *M. elsdenii* strain CH4 deposited at NCIMB, Aberdeen, Scotland, UK under number NCIMB 41125, the *M. elsdenii* strain CH3 deposited on Nov. 24, 2010 at NCIMB. Aberdeen, Scotland, UK under number NCIMB 41787, and the *M. elsdenii* strain CH7 deposited on Nov. 24, 2010 at NCNB, Aberdeen, Scotland, UK under number NCIMB 41788.

The *M. elsdenii* strain in accordance with the first and second aspects of the invention is further characterized by its:
- ability to utilize lactate very efficiently even in the presence of sugars;
- resistance to ionophores;
- relatively high growth rate;
- capability to produce predominantly acetate; and
- capability to proliferate at relatively low pH values below 5.0 and as low as 4.5.

According to a third aspect of the invention there is provided a composition for facilitating the adaptation of ruminants from a roughage-based diet to a high-energy concentrate-based diet, the composition consisting essentially of the bacterial culture of the first or second aspects of the invention.

According to a fourth aspect of the invention there is provided a method of facilitating the adaptation of ruminants from a roughage-based diet to a high-energy concentrate diet including the step of administering to the rumen of said ruminants an effective amount of a bacterial culture according to the first or second aspects of the invention.

According to a fifth aspect of the invention there is provided a feed-additive for ruminants comprising a carrier and an effective amount of a bacterial culture according to the first or second aspects of the invention.

Preferably the culture is disposed in an anaerobic container.

According to a sixth aspect of the invention there is provided a method for the treatment of ruminal lactic acidosis and prevention of any one or more of the following, namely ruminal lactic acidosis, rumenitis, ruminal lactic acidosis induced laminitis, ruminal lactic acidosis induced bloat and liver abscesses, including the step of anaerobically administering to the rumen of a ruminant an effective amount of a bacterial culture according to the first or second aspects of the invention.

According to a seventh aspect of the invention there is provided a veterinary agent for the treatment of ruminal lactic acidosis and prevention of any one or more of the following, namely ruminal lactic acidosis, rumenitis, ruminal lactic acidosis induced laminitis, ruminal lactic acidosis induced bloat and liver abscesses, comprising an effective amount of a bacterial culture according to the first or second aspects of the invention.

According to an eighth aspect of the invention there is provided a preparation for the treatment of ruminal lactic acidosis and prevention of any one or more of the following, namely ruminal lactic acidosis, rumenitis, ruminal lactic acidosis induced laminitis, ruminal lactic acidosis induced bloat and liver abscesses in ruminants comprising:
- an inoculum of a bacterial culture according to the first or second aspects of the invention; and
- a separate anaerobic growth medium, the components of the preparation being disposed in separate chambers of an anaerobic container which are anaerobically connectable to each other, thus to inoculate the growth medium with the culture anaerobically.

According to another aspect of the invention there is provided a method of achieving any one or more of the following improvements in ruminants namely:
- increased milk production;
- improved feedlot performance;
- improved growth rate;
- decrease in finishing time;
- lower digestive morbidity and mortality;
- lower incidence of lactic acidosis and related diseases;
- improved feed conversion efficiency; and
- capability to feed on relatively higher concentrate diets, including the step of administering to the rumen of a ruminant an effective amount of a bacterial culture according to the first or second aspects of the invention.

Preferably the culture is administered anaerobically.

According to yet another aspect of the invention there is provided a method of isolating a biologically pure culture of a superior ruminal microorganism in a relatively shorter time period than conventional methods, the method including the steps of:
- obtaining a sample of ruminal fluids; and
- cultivating the sample on a pre-selected growth medium, the method being characterized in that a plurality of parameters selected from the group comprising growth medium constituents, dilution rate, pH, temperature anti-microbial agents, gaseous environment, redox potential, lack of nutrients and challenging organisms, are pre-selected to favor the superior rumen microorganism to the detriment of inferior rumen microorganisms.

The invention will now be described in more detail below with reference to the below examples and the enclosed drawings wherein.

Figure 1:
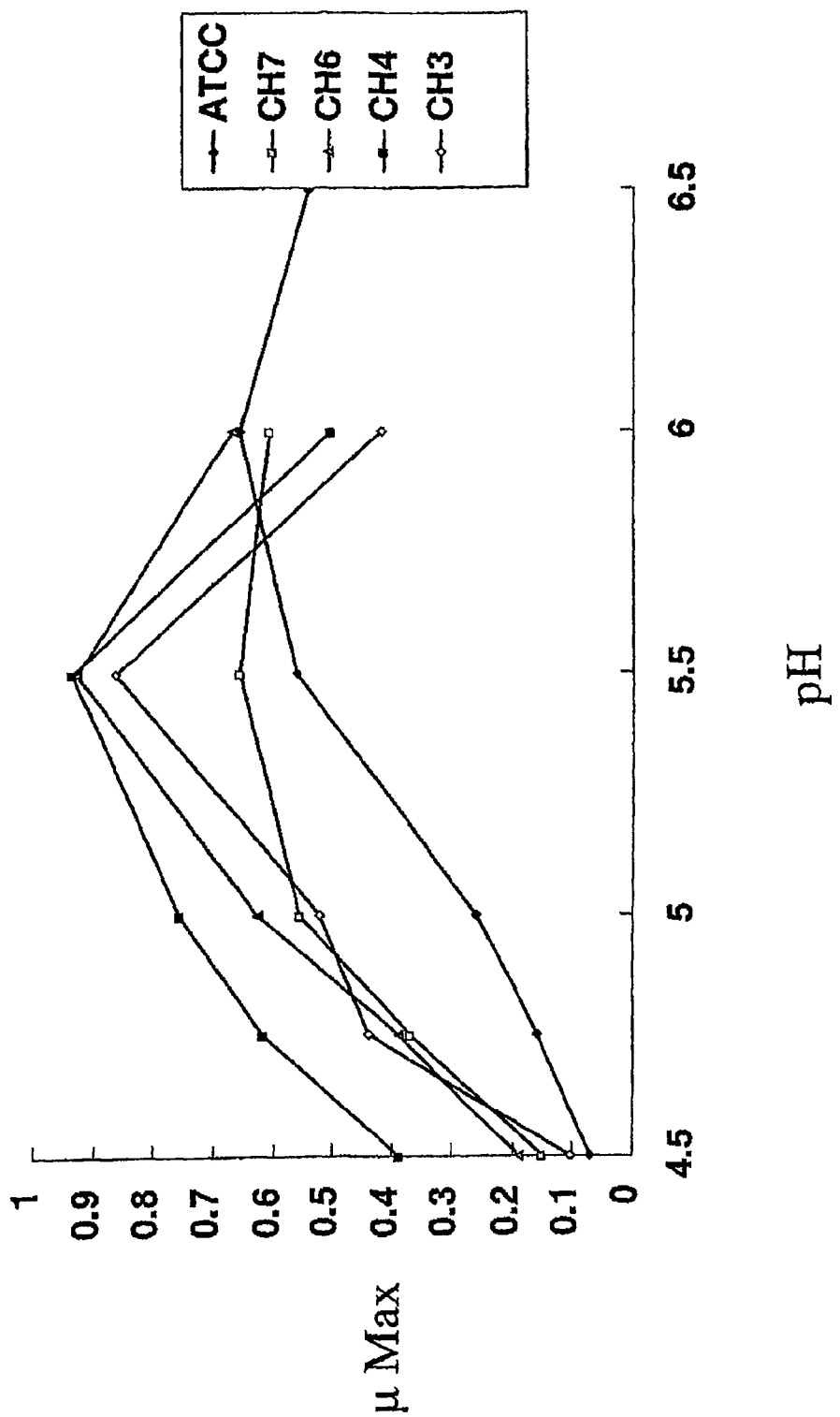
FIG. 1 is a graph of growth rates of lactate utilizes at various pH values.

In accordance with the present invention, organisms capable of utilizing lactic acid were isolated directly from ruminants adapted to a high-concentrate diet. The objective was to select those cultures with the best combination of characteristics for the purpose of application as mass-cultured, preserved inocula for prophylactic and/or therapeutic treatment of lactic acidosis.

For the lactate-utilizing bacteria to be effective they must be highly active and adapted to multiplication in the rumen of animals on high-concentrate diets. The organisms should be able to multiply at pH values below pH 5.0. The selected isolates should also be resistant to ionophore antibiotics commonly added to feedlot diets. Lactate should be preferentially used as a carbon source even in the presence of soluble carbohydrates such as glucose and maltose, which would be present in high proportions in high-concentrate diets.

METHODS

1. Animals Used During Isolations

Samples of rumen contents from animals with a pre-selection for lactate utilizing bacteria were chosen, namely lactating fistulated dairy cows at the Dairy Cow Nutrition unit, Irene, of the Agricultural Research Council (South Africa), as well as feedlot cattle of Chalmar Beef (Pretoria, South Africa) which were slaughtered at the end of their finishing periods. All the animals were adapted to high-concentrate diets, which increased the numbers of naturally occurring lactate utilizing bacteria.

2. Sample Collection and Preparation

Samples of rumen contents were collected from dairy cows at about 09h00, after the cows had been fed and milked. Samples of rumen contents from feedlot animals were obtained 15-30 minutes after the animals had been slaughtered. Plastic screw-cap sample bottles were filled to capacity with rumen fluid filtered through two layers of cheesecloth. The rumen fluid was transferred directly into the fermenter.

3. pH-auxostat

A New Brunswick Scientific Bioflo 1 continuous culture system was modified into a pH-auxostat by converting the pH-dosing pump to a medium addition pump. The pH was monitored with a Schott S23158 pH-electrode connected to a Digital Data Systems 302 pH-meter and titrator. A poorly buffered medium was added whenever the pH increased over the set value until the desired value was reached. The working volume of the culture vessel was 270 ml. The maximum dilution rate obtained for a given organism during auxostat cultivation is a measure of the maximum growth rate of that organism during that condition.

4. Isolation of Lactate Utilizing Rumen Bacteria via the Auxostat 4.1 Growth Conditions and Medium Filtered rumen fluid was used to fill the fermenter (270 ml) initially and the titrator activated to add sterile medium (Medium 1) to the culture proportionally to the increase in pH of the culture. Medium 1 was a semi-defined rumen fluid free medium consisting of: Na-lactate (70%), 10 g/l; Peptone, 2 g/l; $KH_2PO_4$ 1 g/l; $(NH_4)_2SO_4$ 3 g/l; $MgSO_4$ $7H_2O$ 0.2 g/l; $CaCl_2.2H_2O$ 0.06 g/l; Vitamins (Pyridoxolhydrochloride, 4 mg/l; Pyridoxamine, 4 mg/l; Riboflavin, 4 mg/l; Thiaminiumchloride, 4 mg/l; Nicotinamide, 4 mg/l; Ca-D-pantothenate, 4 mg/l; 4-Aminobenzoic acid, 0.2 mg/l, Biotin, 0.2 mg/l, Folic acid, 0.1 mg/l and Cyanocobalamin, 0.02 mg/1); $Na_2S.9H_2O$, 0.25 g/l; Cysteine, 0.25 g/l; Antifoam, 0.07 ml/l and Monensin, 10 mg/l. The Na-lactate and mineral solution were both added to the reservoir boffle and autoclaved for 60 min. The peptone was dissolved in 300 ml $d.H_2O$ and autoclaved separately in a 1.0 l Schott bottle with a bottom outlet fitted with Quick-fit glass connections. The vitamin solution was filter sterilized beforehand as well as the two reducing agents. Following autoclaving, the reservoir bottle was gassed with anaerobic gas overnight and the other constituents added separately after cooling. The pH was adjusted to the desired value with 5N HCl.

Continuous culturing followed until a pure culture was observed microscopically. A sample was taken from the fermenter with a sterile syringe, which was sealed and transferred into the anaerobic cabinet (Forma Scientific model 1024). One droplet of the culture was streaked out in a Petri dish containing Medium 1 solidified with 2% agar. Incubation followed at 39° C. overnight and a single colony was transferred with a sterile needle and syringe into a fresh Medium 1 contained in a 30 ml serum bottle. After incubation at 39° C. for 24 h the culture was transferred to several slants containing Medium 1 and incubated overnight. These slants were stored above liquid nitrogen for long-term preservation.

4.2 Batch Growth Rates of Isolates in Fermenter

The growth rates of the isolates were verified using the batch cultivation technique and monitoring the increase in optical density over time. The natural log of the optical density (OD) was plotted against time and the linear part of the graph was used to determine the slope, which represented the maximum growth rate of the organism. Determination of the batch growth rate was performed in a chemostat culture, which was diluted with a sterile medium until a very dilute culture suspension was obtained and the medium supply cut off in order to start the batch growth. The advantage of using a chemostat culture for this work is that there is no lag phase since the cells are all viable and adapted to the medium.

4.3 Analytical Techniques

Volatile fatty acids were determined by gas chromatography with a Carlo Erba GC4200 gas chromatograph with flame ionization detector and a Tupelo 1-1825 column (Supelco Inc., Bellefonte Pa., USA). Operating conditions were as follows: carrier gas, nitrogen; flame gases, hydrogen and air; column temperature 175° C.; injection port temperature 200° C. A Barspec data system (Barspec Systems Inc., Rehovot, Israel) was used for peak integration. Pivalic acid served as the internal standard. The utilization of the D-and L-lactate isomers were determined enzymatically (Test combination 1112 821, Boehringer Mannheim GmbH, Mannheim).

5. Isolations of Bacteria via Spread Plate Method 5.1 Culture Media

The incubated rumen fluid lactate (IRFL) medium for the spread plate isolations consisted of 400 ml incubated clarified rumen fluid (Olumeyan et al., 1986) from lucerne-fed sheep, 371 ml distilled water, 2 g peptone (Merck), 15 g agar, 100 ml 10% (w/v) sodium-D, L-lactate solution, 100 ml 0.04% (w/v) bromocresol purple solution and 25 ml mineral solution containing 40 g/l $KH_2PO_4$; 120 g/l $(NH_4)_2SO_4$; 8 g/l $MgSO_4.7H_2O$ and 2.4 g/l $CaCl_2.2H_2O$. Lactic acid (90% w/v) was used to adjust the pH to 5.5 before autoclaving at 121° C. for 25 minutes. After sterilization the medium was cooled down in a 50° C. water bath while being gassed with an anaerobic gas mixture. Two milliliters of each of the reducing agents, $Na_2S.9H_2O$ (12.5% w/v) and $cysteine.HCl.H_2O$ (12.5% w/v) were added aseptically. As IRFL medium is not completely selective for lactate-utilizes, bromocresol purple was incorporated to facilitate detection of lactate-utilizes. When lactate is utilized there is a change in ionic balance in the immediate vicinity of the colony causing a pH increase. A rise in pH above 6.3 was indicated as a color change from yellow to purple in the zone concentric with the culture.

Acid tolerance was determined on IRFL agar plates with initial medium pH values of 4.5, 5.0 and 5.5.

Resistance to ionophores was tested on IRFL agar plates containing 10 ppm of ionophores generally used in high-concentrate diets i.e. monensin (Sigma) and lasalocid (Sigma). Repression of lactate utilization by soluble sugars was tested on IRFL agar plates supplemented with maltose or glucose at a final concentration of 10 g/l. A positive result i.e. a purple zone concentric with the colony indicated that the rate of base release due to lactate utilization exceeded that of acid production from the added sugar. The isolates were also screened on IRFL agar medium without lactate, but to which glucose or maltose had been added at a concentration of 10 g/l, to determine utilization of the two sugars.

Growth rates on maltose and glucose were determined on media similar to SDL medium, but in which the lactate was replaced with either 10 g/l glucose or maltose.

5.2 Spread Plate Isolations and Screening

The samples for the spread plate isolations were diluted (Mackie & Heath, 1979) in an anaerobic cabinet. Spread plates of IRFL medium were prepared with the $10^{-4}$ to $10^{-6}$ dilutions and incubated anaerobically at 39° C. After 24 hours, well-spaced colonies showing a purple zone were transferred to IRFL liquid medium in 1.5 ml microtubes. The inoculated microtubes, which showed a color change to purple within 16 hours, were screened for acid tolerance, ionophore resistance, catabolite repression and utilization of glucose and/or maltose. Screening was done by replica plating (Lederberg & Lederberg, 1952) using a multipoint inoculator to inoculate 20 isolates onto a set of nine agar plates of different compositions described above.

5.3 Growth Rate Determinations

Growth was measured, in triplicate, in SDL, SDG or SDM medium as an increase in turbidity at 578 nm. Vials were incubated in a water bath at 39° C. between readings. Readings were continued until the turbidity reached the limit of a satisfactory relationship with biomass. The natural logarithms of optical density (OD) were plotted against incubation time. The slope of the exponential growth phase that represents the specific growth rate was calculated by linear regression with the aid of a spreadsheet software package.

The cultures grown on SDL medium at pH 5.7 were then incubated further for a total of 24 hours after which 9 ml was preserved by the addition of one milliliter 10% (w/v) NaOH for analysis of end-products formed and utilization of lactate isomers.

5.4 Growth Physiological Studies of Plate Isolates

Fermenter description. A continuous culture system was set up with three fermenters with a capacity of about 250 ml each. A single peristaltic pump was used to supply medium at different rates to the three fermenters. Temperature of the cultures was maintained at 39° C. The medium and fermenters were gassed with 100% $CO_2$ to maintain an anaerobic environment. The pH of the cultures was maintained at pH 5.5 by addition of 20% (w/v) orthophosphoric acid as required. The dilution rate was set at 70%, 80% and 90% of maximum growth rate. A sample of 80 ml was withdrawn aseptically from each fermenter at steady state. From this sample the dry mass of the cells and the residual lactic acid in the medium was determined. The biomass output rate, a product of the dilution rate and steady-state biomass, was calculated using the actual dilution rate and the dry mass figures. The growth yield coefficient, which is a function of the biomass concentration at steady state over the amount of substrate utilized, was calculated using lactic acid residue and dry mass figures.

6. Trials with Sheep to Evaluate the Ability of Isolate CH4 to Prevent Ruminal Lactic Acid Accumulation

6.1 Methods

In the first trial 12 ruminally-cannulated wether sheep (mean live weight ca 40 kg) were randomly divided into a treatment and a control group, each comprising six animals. All animals were fed roughage ad lib for 21 days. On day 21 they were fasted for 11 hours prior to being offered 1000 g of maize meal/animal and at the same time being dosed intra-ruminally with 300 g of maltose syrup/animal. One hour later all maize not yet consumed by each animal was packed directly into its rumen. Immediately thereafter animals in the treatment group were dosed intra-ruminally with $1 \times 10^{11}$ cfu of CH4, whilst animals in the control group were similarly dosed with cell-free filtrate of CH4 preparation, i.e. CH4-free. Samples of rumen fluid were taken at two-hourly intervals, up to 12 h post dosing, for determination of rumen lactic acid concentration.

In the second trial another group of 12 ruminally-cannulated wethers, mean live weight 29 kg, with no previous exposure to concentrate feeding, were used.

They had random access to ground *Eragrostis teff* hay and a protein-mineral lick. Lambs were randomly divided into two groups of six animals each, namely a treatment and a control group. On the first day of the experiment (Day 1) all lambs received the following diet ad lib: maize, 888; molasses, 69; urea, 17; limestone, 11; dicalcium phosphate, 6; salt, 4; ammonium sulphate, 4; mineral-vitamin premix with monensin, 1 (g/kg DM). On day one of concentrate feeding each animal in the treatment group received a dose of CH4 intra-ruminal at 12:00, i.e. 3h post feeding. Animals in the control group were similarly dosed with water. Rumen samples were obtained at various times on the day prior to the start of concentrate feeding (Day-1) and on the $1^{st}$, $2^{nd}$, $3^{rd}$ and $7^{th}$ days of concentrate feeding, for determination of ruminal lactic acid concentrations.

7. Evaluation of Isolate CH4 in High Producing Dairy Cows

7.1 Cultivation of Lactate Utiliser for the Animal Trial

A Braun Biostat B fermenter with a working volume of 10 liters was transformed into a chemostat using a Watson-Marlow 505S dosing pump equipped with a 55 rpm drive for transporting sterile medium from 50 liter stainless steel kegs. The working volume was kept constant by continuously transferring excess of culture above the 10-liter level of the fermenter via a dip tube and a peristaltic pump (Watson-Marlow 505S) to a 50 liter polypropylene Carboy that was cooled in a chest freezer. The delivery rate of this harvest pump was set to approximately 120% of the medium supply pump. The excess of volume removed from the fermenter consisted of anaerobic gas from the headspace.

A tangential flow filter system (Millipore Pellicon) equipped with a Millipore HVMP 0.45 micrometer (15 ft$^2$) filter and a Millipore Masterflex Easy-Load peristaltic pump, was used for concentrating the culture.

The medium used was CSL4. The vitamin, reducing agent, mineral and trace element solutions were filter sterilized prior to addition to the medium reservoir. Following autoclaving, the reservoir was gassed with anaerobic gas.

The production approach was a staggered type of production. Two consecutive productions were performed, each producing enough cells for the treatment of one day's group of animals. The number of concentration steps was limited to one per production as each day's production was collected into a 50 liter vessel. The dilution rate of the culture was 0.4 $h^{-1}$ and the "down time" between batches was 50 minutes. A backup run consisting of 45 liters was started prior to the first day's production, which also served to promote the chemostat culture into steady state.

7.2 Experimental Animals

Sixty high producing dairy cows were blocked according to milk production during previous lactation and body weight and thereafter randomly allocated, within each block, to one of the following treatments: 1) Control diet 60% concentrate; 2) Control diet 60% concentrate+CH4; 3) Control diet 70% concentrate; 4) Control diet 70% concentrate+CH4. Cows were dosed with organism CH4 at calving, 10 days post partum and 20 days post partum.

The following parameters were monitored:
1. dry matter intake daily;
2. milk production daily;
3. milk fat, protein and lactose weekly; and
4. body weight and condition score monthly.

8. Statistical Analyses

Data were analyzed by analysis of variance for a completely randomized block design using the program Genstat 5. Previous lactation milk productions were used as a covariate and milk production was reported as covariate adjusted values. Contrasts were used to determine the significance of difference among treatments as follows:

+CH4 or −CH4 (dosed vs. non-dosed)

Control diet 70% concentrate vs. control diet 70% concentrate +CH4

Control diet 60% concentrate vs. control diet 60% concentrate +CH4

Differences were declared significant at P<0.10 and trends were declared at P<0.15 unless otherwise noted.

9. Effects of *Megasphaera elsdenii* Supplementation on Animal Health and Feedlot Performance A homogenous group of 448 Bonsmara weaner steers (average initial live weight 215 kg) were randomly assigned to eight experimental treatments in a 2×2×2 factorial design, with factors (1) CH4 addition (yes or no); (2) ionophore addition (yes or no); and (3) roughage level (high or low). The feedlot diets used and the dietary regime followed were as follows:

Ingredient composition of experimental diets, at the end of the adaptation period (day 14 to end):

| Ingredient | Inclusion (%, on as-fed basis) | |
| --- | --- | --- |
|  | High-roughage | Low-roughage |
| *Eragrostis* hay | 8.0 | 2.0 |
| Maize meal | 27.0 | 30.0 |
| Hominy chop | 32.0 | 35.0 |
| Molasses meal | 12.0 | 12.0 |
| Brewers grain | 6.0 | 6.0 |
| Wheat bran | 10.0 | 10.0 |
| Cottonseed oilcake | 2.0 | 2.0 |
| Urea | 1.0 | 1.0 |
| Limestone | 1.5 | 1.5 |
| Salt | 0.5 | 0.5 |

Dietary adaptation regime followed from arrival, when animals were given roughage ad lib, until they were on the final feedlot diet:

| Day | Additional hay | Roughage level (%) in the diet | |
| --- | --- | --- | --- |
|  |  | High-roughage | Low-roughage |
| 1-2 | Ad lib | 18 | 12 |
| 3-4 | None | 18 | 12 |
| 5-7 | None | 14 | 8 |
| 8-10 | None | 12 | 6 |
| 11-13 | None | 10 | 4 |
| 14 to end | None | 8 | 2 |

Nutrient composition of the final feedlot diets used (% of as-fed):

| Nutrient | High-roughage | Low-roughage |
| --- | --- | --- |
| Dry matter | 89.6 | 89.8 |
| Crude protein | 14.4 | 13.4 |
| Starch | 33.5 | 35.9 |
| NDF fibre | 26.9 | 23.9 |
| ADF fibre | 9.5 | 8.7 |
| Fat | 4.6 | 4.8 |

Animals were kept in small experimental feedlot pens. There were 7 pens per treatment and 8 animals per pen. Feedlot diets were fed once daily in the morning, at an ad-lib level. All steers were processed upon arrival (standard feedlot procedures) and fed only long roughage for a few days until they were dosed with either CH4 (treatment) or a similar amount of water (controls). During this dosing a 200 ml suspension of CH4 in medium was applied as an once-off oral drench to each treatment animal.

The CH4 culture was prepared by inoculating a 17.5-liter batch of sterile CSL6 medium (starting pH of 5.20) with 1000 ml of fresh inoculum of CH4, pumped directly from fermenter to Carboy container and incubated at 39° C. overnight. The pH of the culture was 6.63 after cultivation and remained the same after 48 hrs. Counts were done on the CH4 culture, after incubation. A peristaltic pump was used to transfer the 200 ml dosage per os to the animal in 10 seconds from the 20-liter carboy.

CSL 6 medium as a 20 liter batch for cultivation of CH4:

|  | 17.5 Litres |
| --- | --- |
| CSL 6 Medium (Sterilized: 55 minutes) | |
| Na-lactate | 971.25 g |
| Indigocarmine | 17.5 ml |
| Trace Mineral solution | 8.75 ml |
| Mineral solution 5 | 87.5 ml |
| Peptone | 17.5 g |
| Yeast extract | 17.5 g |
| CSL | 598.5 g |
| Distilled $H_2O$ | 10688.2 g |
| 10 N KOH (pre-dissolved in 5 l $H_2O$) | 58.3 ml |
| Filter sterilize and added prior to inoculation | |
| Vitamin solution | 35 ml |
| L-cysteine | 35 ml |

Feed intake was determined for each pen (daily/weekly) and individual animal weights were determined (weekly/bi-weekly). These were used to calculate feed conversion ratio (per pen). Animals were observed daily and any animals showing signs of acidosis (diarrhoea, bloating, depression) were removed and treated before returning them to their respective pens right away.

Statistical Analyses

Data were analyzed using the program GenStat 5. Animals were blocked by weight group. The effects of CH4, ionophore and roughage level were tested by means of a 2×2×2 factorial design in an analysis of variance (ANOVA). The data was acceptably normal with homogenous treatment variances. Treatment means were separated using Fishers' protected t-test least significant difference (LSD) at the 5% level, provided that the F-probability from the ANOVA was significant at 5%.

10. Identification of Isolates using Phylogenetics, Based on 16S rRNA Gene Sequences.

10.1 Bacterial Isolates and Culture Conditions.

*M. elsdenii* isolates CH4 and CH7, originally isolated from dairy cows (Wiederhold, 1994) were provided by the inventors. The type strain of *M. elsdenii*, ATCC 25940, was obtained from the American Type Culture Collection. The strains were cultivated in SDL medium as described previously and presumptively identified as *Megasphaera elsdenii* (Wiederhold, 1994).

10.2 Amplification and Sequencing of 16S ribosomal RNA Genes.

Genomic DNA was extracted from bacterial cells using standard procedures (Ausubel et al., 1988). The primers used to amplify the 16S rRNA genes were selected from universally conserved regions in all eubacteria (Table 1). PCR was carried out using primers FD1 (covering positions 8 to 26) and R11 (positions 1384-1400). All target positions of primers used for amplification and sequencing refer to the *E. coli* numbering system (Brosius et al., 1978). The PCR reaction mixture of 100 µl contained approximately 200 ng of DNA, 1 µM of each primer, 200 µM of each nucleotide (dATP, dCTP, dGTP and dTTP), 50 mM KCl, 10 mM Tris-HCl (pH 8.4) and 2.5 mM MgCl and 2.5 U of Taq polymerase (Boehringer Mannheim, Germany). The mixture was overlaid with liquid paraffin to prevent evaporation. The thermal profile consisted of 30 cycles of denaturation for 1 minute at 94° C., annealing at 45° C. for 2 minutes and subsequent extension at 72° C. for 3 minutes in a thermal cycler (Hybaid, U.K). Final extension was carried out at 72° C. for 6 minutes. The homogeneity of the amplicons was analyzed by agarose gel electrophoresis (Sambrook et al., 1989). The PCR product was excised from the gel and purified using the Wizard PCR Preps kit (Promega, U.S.A.) as prescribed by the manufacturer. Direct sequencing of double stranded PCR amplicons and subsequent separation of sequencing reaction products on polyacrylamide gels were essentially carried out according to the protocol of Dorsch and Stackebrandt (1992). Sequencing primers are listed in Table 1.

TABLE 1

Primers used to amplify and sequence the 16S rRNA gene. Primer sequences have been published previously (Dorsch and Stackebrandt, 1992; Lane et al., 1985; Stackebrandt and Charfreitag, 1990; Hutson et al., 1993). A combination of these primers covered a total of 1419 nucleotides of the 16S rRNA gene.

| Primer Primer Sequence (5' to 3') | Primer Target position[a] Primer sequence (5' to 3') | Primer Target position[a] Primer sequence (5' to 3') |
|---|---|---|
| Reverse direction (antisense) | | |
| R11 (PCR) | 1384-1400 | CGGTGTGTACAAGGCCC [SEQ ID: NO: 1] |
| R1193 | 1174-1192 | CGTCATCCCCGCCTTCCTC [SEQ ID: NO: 2] |
| R1353 | 1336-1352 | CGATTACTAGCGATTCC [SEQ ID: NO: 3] |
| R961/R7 | 949-963 | TCGAATTAAACCACA [SEQ ID: NO: 4] |
| R5 | 786-802 | CTACCAGGGTATCTAAT [SEQ ID: NO: 5] |
| R361/R1 | 340-355 | CTGCTGCCTCCCGTAGG [SEQ ID: NO: 6] |
| Forward direction (sense) | | |
| FD1/F1 (PCR) | 8-26 | AGAGTTTGATCCTGGCTCA [SEQ ID: NO: 7] |
| F1353 | 1336-1352 | GGAATCGCTAGTAATCG [SEQ ID: NO: 8] |
| F361 | 340-355 | CCTACGGGAGGCAGCAG [SEQ ID: NO: 9] |
| F961 | 949-963 | TGTGGTTTAATTCGA [SEQ ID: NO: 10] |

[a]All target positions for primers refer to *E. coli* numbering systems (Brosius et al., 1978).

10.3 Data Analysis.

The 16S rDNA sequences obtained were automatically aligned with sequences obtained from the Ribosomal Database Project (RDP; Maidak et al., 1996) using the alignment program CLUSTALW (Genetics Computer Group, 1991). Sequences in the profile were trimmed in order to standardize with regard to the size of the sequences of each organism included in the alignment profile. A total of 1388 nucleotide sequence positions were included in the profile. Published sequences of a number of organisms occurring in the rumen were included in the alignment profile (Table 2). Ambiguous sequences in the alignment profile were manually aligned using the Genetics Data Environment (GDE) alignment editor (Smith, 1992). For inferring phylogenetic relationships, the program fastDNAml (Olsen et al., 1994) was used, which is based on the maximum likelihood algorithm (Felsenstein, 1981). A phylogenetic tree was constructed using the program Treetool (GDE). *Escherichia coli* and *Acinetobacter calcoaceticus* served as out groups in the construction of the tree.

TABLE 2

Organisms included in the alignment profile using the programs CLUSTALW.
All the sequences were retrieved from the RDP and the Genbank databases.

| | |
|---|---|
| Lactobacillus ruminis ATCC 27780 | Streptococcus bovis ATCC 33317 |
| Fibrobacter succinogenes S85 ATCC 1916 | Methanobrevibacter ruminantium ATCC 35063 |
| Megasphaera elsdenii ATCC 17752 | Methanobacterium formicicum DSM 1312 |
| M. elsdenii ATCC 25940 | Methanosarcina barkeri DSM 1538 |
| M. elsdenii CH4 | Methanomicrobium mobile ATC 35094 |
| M. elsdenii CH7 | Prevotella ruminicola ATCC 19189 |
| M. cerevisiae | Wolinella succinogenes ATCC 33913 |
| Synergistes jonesii | Escherichia coli |
| Clostridium acetobutylicum ATCC 824 | Acinetobacter calcoaceticus ATCC 33604 |
| Eubacterium cellulosolvens ATCC 43171 | Quinella ovalis |
| Eubacterium uniformis ATCC 35992 | Selenomonas ruminantium GA192 |
| Clostridium polysaccharolyticum ATCC 33142 | Eubacterium limosum ATCC 8486 |

RESULTS

Auxostat Isolations

Isolation of Lactate Utilizing Bacteria in Auxostat

Isolation 1: The rumen contents, obtained from cow 8710, filling the culture vessel of the fermenter were immediately exposed to fresh sterile selective medium when the auxostat was triggered by an increase in pH. Initial dilution rates were in the region of 0.53 $h^{-1}$ for the first 2 hours at pH 5.30. During the following two hours the dilution rate increased to 0.65 $h^{-1}$. In order to increase the specificity of the isolation the pH was decreased to pH 5.0, which resulted in a decrease in dilution rate to 0.37 $h^{-1}$. Cultivation was continued for a further 24 hours after which time only two morphological types could be detected in the enrichment culture. The dilution rate decreased slightly as the cultivation time increased after the initial 24-hour period and at the end of the isolation the dilution rate was only 0.33 $h^{-1}$.

A sample of the fermenter contents was streaked onto agar medium, in the anaerobic cabinet, and a single colony containing a pure culture was transferred to agar slants and preserved over liquid nitrogen and this culture was denoted as Isolate CH1.

Isolation 2: During this isolation from rumen contents of cow 8812 a dilution rate of 0.25 $h^{-1}$ was observed for the first 24 hours and during the subsequent 24-hour period the dilution rate was between 0.34 and 0.41 $h^{-1}$. After 48 hours of cultivation it was not clear whether a "pure" culture had been obtained and the cultivation proceeded for a further 24 hours. The dilution rate during this period was 0.41 $h^{-1}$ and a pure culture was isolated from the fermenter via a colony from a Petri dish. This isolate was designated Isolate CH2.

Isolation 3: The dilution rate during this isolation period decreased from, 0.28 to 0.21 $h^{-1}$ over a 48-hour period. The isolate obtained from the rumen of cow 8708 was designated Isolate CH3.

Isolation 4: Initial dilution rates were in the order of 0.38 $h^{-1}$, but within 4 hours the dilution rate decreased to 0.276 $h^{-1}$ and at the end of the 48-hour period the dilution was only 0.197 $h^{-1}$. The isolate obtained during this isolation from the rumen content of cow 8826 was designated CH4.

Isolation 5: At the end of the isolation period a spore former was the dominant organism and the experiment was terminated.

Isolation 6: During this isolation the dilution rate decrease following the same pattern as for the other isolations and the final dilution rate was only 0.116 $h^{-1}$. The isolate was obtained from rumen contents of feedlot cattle and was designated CH6.

Isolation 7: The rumen contents used during this isolation were obtained from feedlot cattle. The dilution rates decreased from 0.142 to 0.106 $h^{-1}$, during the first seven hours of isolation. The isolate obtained was designated CH7.

Medium Modification for Chemostat Studies

A consistent decrease in dilution rates was observed during the isolation of the lactate utilizes, which indicated that the formulation of the medium was not optimal. During the first 24 hours of isolation 7 the dilution rate decreased from 0.142 to 0.106 $h^{-1}$. A pulse dose of 5 ml sterile rumen fluid was added directly into the fermenter and after 4 hours the dilution rate peaked at 0.408 $h^{-1}$. Thereafter the dilution rate slowly decreased to 0.15 $h^{-1}$. This "pulse and shift" technique demonstrated that the medium was nutritionally deficient.

Another "pulse and shift" experiment with 1 ml vitamin solution resulted in a dilution rate peak of only 0.28 $h^{-1}$. However, a larger vitamin pulse resulted in a dilution rate peak of 0.497 $h^{-1}$, which was higher than with the rumen contents pulse. Lactate utilization reflected the same results namely, respective b-and L-lactate isomer utilization of 22 and 86% without extra vitamins, and with extra vitamins respectively 68 and 91%. Medium 1 listed in the Methods reflect the modified version with higher concentrations of the vitamins. During another "pulse and shift" experiment it was established that yeast extract increased the cell yields of the isolates.

Growth Rates of Megasphaera elsdenii ATCC 25940 and auxostat isolates vs. pH

Growth rates of the bacteria were determined with the pH-auxostat at various pH values between 4.5 and 6.5, using the modified lactate medium. These growth rates were checked against the values obtained during batch cultivation at the specific pH values and the average value was used.

Megasphaera elsdenii ATCC 25940, the type strain, showed an increase in growth rate from pH 4.5 up to pH 6.0, followed by a rapid decrease in growth rate at pH 6.5 (FIG. 1). The maximum growth rate achieved by ATCC 25940 was 0.66 $h^{-1}$, which corresponds to the reported growth rate of 0.6 $h^{-1}$ by Therion et al. (1981).

All the isolates outperformed ATCC 25940 as far as maximum growth rate was concerned, especially at pH values of 5.5 and below (FIG. 1). The maximum growth rates of the isolates all peaked at pH 5.5 with respective growth rates, ($h^{-1}$) of 0.66, 0.93, 0.938 and 0.864 for isolates CH7, CH6, CH4 and CH3. Of all the isolates, CH4 proved to be the most acid tolerant with a growth rate of 0.389 $h^{-1}$ at pH 4.5, and the organism with the second best acid tolerance, CH6, with a growth rate of only 0.19 $h^{-1}$ at pH 4.5. A sharp decrease in growth rate between pH 5.5 and 6.0 was observed for three isolates, namely CH6, CH4 and CH3. Isolate CH7 had only a slight variation in growth rate between pH 5.0 and 6.0, which resembles ATCC 25940 between pH 5.5 and 6.5.

Growth Rates of Auxostat Isolates on Glucose

Figure 2:
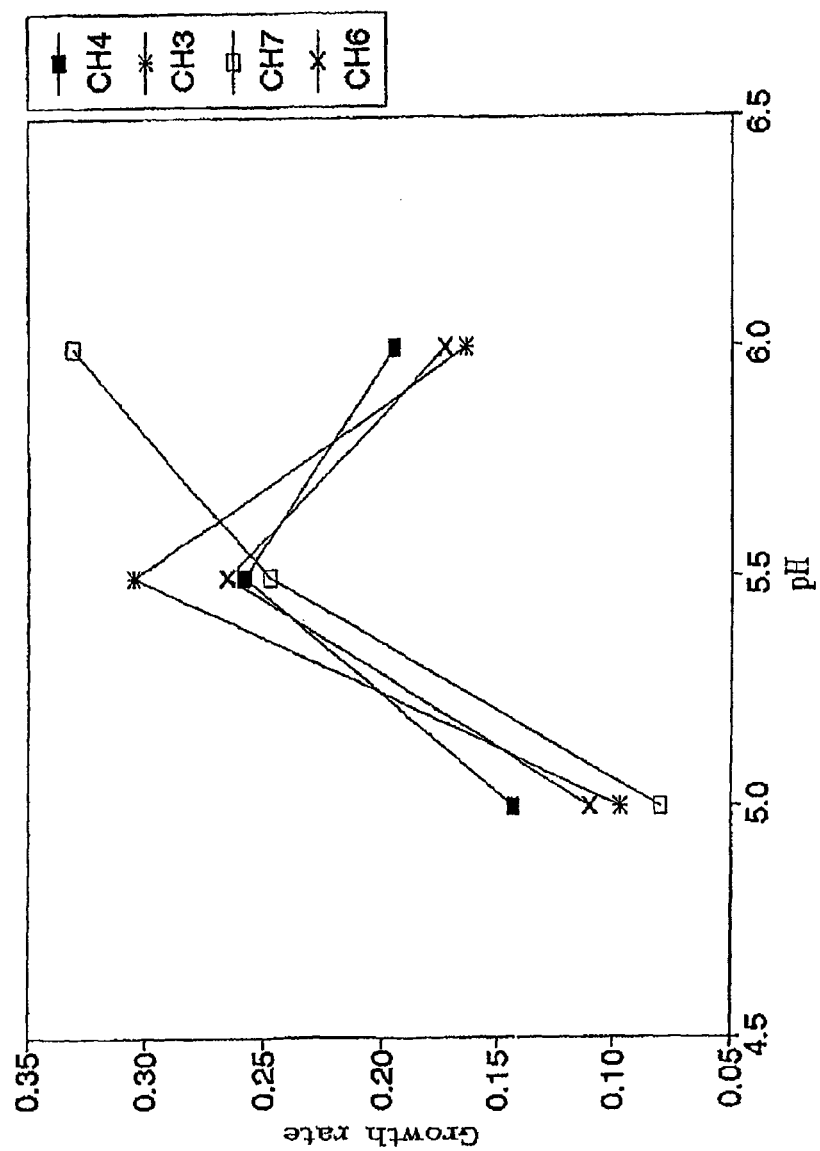
FIG. 2 is a graph of the growth rates ($h^{-1}$) of the lactate utilizing isolates, on glucose medium at various pH values.

The growth rates of three isolates were determined at pH 5.0, 5.5 and 6.0, using the fed-batch growth technique (FIG. 2). Growth rates were noticeably lower for all three isolates on glucose compared to lactate. The most promising isolate on lactate, namely CH4 achieved a maximum growth rate of only 0.25 $h^{-1}$ at pH 5.5 on glucose, compared to 0.938 $h^{-1}$ on lactate. Isolate CH7 achieved the highest growth rate (0.33 $h^{-1}$) on glucose at pH 6.0 amongst the isolates.

Conversion of Lactate by Isolate CH4

Isolate CH4 was cultivated at three chemostat dilution rates, namely 0.94, 0.83 and 0.75 $h^{-1}$ on lactate medium. During steady state, samples were taken and analyzed for volatile fatty acids (VFA) and the utilization of lactate determined. Batch cultivation was also conducted and samples were taken at stationary phase. Samples of the sterile medium were also analyzed for VFAs and lactate.

With an increase in dilution rate the relative production of fatty acids changed, namely at low dilution rates more butyrate and valerat were produced and less propionate and acetate (Table 3). At the highest dilution rate very small amounts of butyrate were produced, with no valerat and only slightly more acetate and propionate. Lactate utilization decreased as expected, with an increase in dilution rate. During the cultivation D=0.75 more than 40% of the lactate was converted to VFAs and although lactate utilization was high, a large proportion of the available energy was wasted. When CH4 was cultivated in batch it produced mainly acetate and propionate. The concentrations of VFAs produced during batch cultivation were much lower than expected and the only explanation would be that CH4 utilizes the VFAs when lactate is depleted.

TABLE 3

Volatile fatty acids produced by isolate CH4 from lactate during chemostat cultivation at various dilution rates and during batch cultivation.

| Dilution rate ($h^{-1}$) | Volatile fatty acids (mM) | | | | % Lactate utilised |
|---|---|---|---|---|---|
| | Acetic | Propionic | n-Butyric | n-Valeric | |
| 0.75 | 7.221 | 5.779 | 11.347 | 6.383 | 92.66 |
| 0.83 | 10.048 | 12.293 | 0.423 | 0.012 | 53.54 |
| 0.94 | 8.529 | 10.517 | 0.271 | 0 | 39.65 |
| Batch | 10.659 | 7.737 | 0.266 | 0 | 97.62 |

Spread Plate Isolations and Screening

More than 800 colonies from nine rumen samples of four dairy cattle and two feedlot cattle were inoculated into IRFL liquid medium in microtubes. Of these 610 produced a color change to purple in the medium within 16 hours of incubation. Nineteen of the screened isolates were chosen for further characterization as they met the specifications required.

Four of the selected isolates, AW09; AW10; AW11 and AW12 were capable of growth at an initial pH of 4.5. The other fifteen isolates all grew at an initial pH of 5.0 and there was further selection here, as those cultures showing suitable characteristics, being the fastest growers at pH 5.0, were selected.

All nineteen isolates were resistant to the ionospheres monensin and lasalocid at concentrations of 10 ppm, utilized lactate in the presence of maltose and glucose and were capable of growth on both glucose and maltose. These nineteen isolates were all Gram-negative cocci (±1.8 micrometers) occurring in pairs or chains.

Physiological Characterization of Isolates

All the AW isolates used both the D- and L-lactate isomers as both isomers were virtually completely utilized after incubation in SDL medium for 24 hours. Results indicated that the isolates comprised a fairly uniform group and therefore only certain isolates were chosen for further characterization. For five of the AW isolates the growth rates on glucose at pH 5.8 ranged from 0.38 to 1.05 $h^{-1}$ with a mean of 0.66 $h^{-}$ (+/− 0.298). The AW isolates tested for VFA production from DL-lactate were found to produce acetic, propionic, n-butyric and n-valeric acids in the following ratio 2:1.5:1:1.3. Some of the AW isolates produced trace amounts of methyl butyric acid. The maximum biomass output rates obtained for the nine isolates ranged from 0.31 to 0.43 g (l.h)$^{-}$. AW15 had the highest biomass output rate and CH4 and AW01 were next in line with 0.39 g (l.h)$^{-1}$. The yield of cell dry mass per gram of lactic acid utilized, ranged from 0.1 to 0.17 for the nine isolates.

Presumptive Identification of Isolates

The isolates obtained were presumptively identified and those meeting the morphological typing as strains of *Megasphaera elsdenii* were used for further characterization.

Trials with Sheep to Evaluate the Ability of Isolate CH4 to Prevent Ruminal Lactic Acid Accumulation Results of the first sheep trial are shown in Table 4.

TABLE 4

Lactic acid concentration in rumen fluid of roughage-fed sheep suddenly challenged with concentrates, and being dosed intra-ruminally with CH4 (treatment) or placebo (control) at the same time.

| Time after CH4 dosing (h) | Lactic acid concentration (g/liter) | |
|---|---|---|
| | CH4 treatment | Control |
| 0 | <0.1 | <0.1 |
| 2 | 0.3 | 1.4 |
| 6 | 0.8 | 3.6 |
| 8 | 0.5 | 5.2 |
| 10 | 0.4 | 6.1 |
| 12 | 0.2 | 5.9 |

Results of the second sheep trial are shown in Table 5.

TABLE 5

Lactic acid concentration in rumen fluid of roughage-fed sheep suddenly changed onto a concentrate diet (ad lib), and being dosed intra-ruminally with CH4 (treatment) or placebo (control) 3 h after first receiving the concentrate diet.

| Day of treatment | Time of day: | Ruminal lactic acid concentration (mMol/liter) | | | |
|---|---|---|---|---|---|
| | | 08:00 | 12:00 | 15:00 | 19:00 |
| −1 | CH4 | 1.4 | 0.7 | 0.6 | 0.7 |
| | Control | 1.5 | 0.9 | 0.5 | 0.7 |
| 1 | CH4 | 0.7 | 0.5 | 2.1 | 2.4 |
| | Control | 0.5 | 0.2 | 1.5 | 1.8 |
| 2 | CH4 | 2.4 | 1.0 | 1.5 | 1.2 |
| | Control | 5.0 | 13.6 | 15.2 | 17.4 |
| 3 | CH4 | 1.6 | 1.0 | 0.7 | 1.0 |
| | Control | 7.8 | 4.5 | 3.5 | 2.5 |
| 7 | CH4 | 1.8 | 1.6 | 1.0 | 1.2 |
| | Control | 2.0 | 1.5 | 2.0 | 1.5 |
| 14 | CH4 | 1.5 | 1.5 | 1.2 | 1.0 |
| | Control | 1.8 | 2.0 | 1.2 | 2.0 |

In both trials dosing with CH4 led to a marked and significant (P<0.001 for both trials) reduction in ruminal lactic acid concentration compared to controls. In both trials control animals showed the expected sharp increase in ruminal lactic acid concentration after abrupt addition of readily fermentable substrate to the rumen. In comparison ruminal lactic acid levels in CH4-treated animals remained more-or-less at pre-substrate-addition levels. This clearly suggested that the lactic acid being produced was largely utilized by CH4.

Evaluation of Isolate CH4 in High Producing Dairy Cows

The most relevant production data is presented in Tables 6 and 7. Data was analyzed separately for all cows (15/treatment) and high producers (10/treatment), respectively.

TABLE 6

Effect of organism CH4 on productivity of lactating dairy cattle from calving to 80 days post partum (all cows).

| | Treatment[1] | | | | Contrast P< | | |
|---|---|---|---|---|---|---|---|
| | | | | | +CH4 vs | 1 vs | 3 vs |
| Parameters | 1 | 2 | 3 | 4 | −CH4 | 2 | 4 |
| Cows per treatment | 15 | 15 | 15 | 15 | — | — | — |
| Dry matter intake kg/d | 24.6 | 24.1 | 23.1 | 22.2 | 0.28 | 0.59 | 0.32 |
| Milk (kg/d) | 36.4 | 34.0 | 33.8 | 32.2 | 0.10 | 0.16 | 0.34 |
| Fat (%) | 3.27 | 3.29 | 3.57 | 3.23 | 0.17 | 0.85 | 0.03 |
| Protein (%) | 3.10 | 3.10 | 3.14 | 3.07 | 0.43 | 0.93 | 0.23 |
| Body Weight | 662 | 608 | 618 | 612 | 0.02 | 0.004 | 0.73 |
| Condition score | 2.80 | 2.48 | 2.45 | 2.28 | 0.06 | 0.08 | 0.36 |

Treatment 1: Control diet, 70% concentrate + CH4
Treatment 2: Control diet, 70% concentrate − CH4
Treatment 3: Control diet, 60% concentrate + CH4
Treatment 4: Control diet, 60% concentrate − CH4

TABLE 7

Effect of organism CH4 on productivity of lactating dairy cattle from calving to 80 days post partum (high producers).

| | Treatment[1] | | | | Contrast P< | | |
|---|---|---|---|---|---|---|---|
| | | | | | +CH4 vs | 1 vs | 3 vs |
| Parameters | 1 | 2 | 3 | 4 | −CH4 | 2 | 4 |
| Cows per treatment | 10 | 10 | 10 | 10 | — | — | — |
| Dry matter intake kg/d | 24.6 | 25.4 | 24.3 | 22.6 | 0.44 | 0.43 | 0.06 |
| Milk (kg/d) | 39.3 | 35.9 | 35.2 | 34.8 | 0.13 | 0.06 | 0.82 |
| Fat (%) | 3.23 | 3.24 | 3.56 | 3.21 | 0.20 | 0.91 | 0.06 |
| Protein (%) | 3.10 | 3.10 | 3.15 | 3.02 | 0.28 | 0.93 | 0.11 |
| Body Weight | 644 | 597 | 623 | 625 | 0.11 | 0.02 | 0.90 |
| Condition score | 2.71 | 2.26 | 2.34 | 2.44 | 0.20 | 0.02 | 0.61 |

Effects of *Megasphaera elsdenii* Supplementation on Animal Health and Feedlot Performance The delivery of live CH4 bacteria per animal averaged $2 \times 10^{11}$ colony forming units per dose per animal throughout the feedlot trials. The most relevant results are presented in Tables 8 to 11. The period of weeks three to five in the feedlot is normally considered the most critical in terms of dietary adaptation. During weeks one and two the diet still has a higher roughage content, which gradually decreases; Intake starts at a comparatively low level and builds up gradually. It is only from week three onwards that the diet is at its lowest roughage level (and highest concentrate level) and intakes are rapidly getting higher. By the beginning of week six animals will normally be considered as adapted to the diet. Week three to five is really the critical period of adaptation of animals to the high-concentrate diet.

TABLE 8

Average daily feed intake (kg as-fed material per animal per day) for CH4-treatment vs control (no CH4 added), for various periods in the feedlot.

| Feedlot period | Treatment | | P-value | s.e. |
|---|---|---|---|---|
| | Plus CH4 | Control (no CH4) | | |
| Week 1-2 | 7.30 | 7.15 | 0.35 | 0.109 |
| Week 3-5 | 10.18 | 10.02 | 0.30 | 0.103 |
| Week 1-13 | 9.64 | 9.50 | 0.29 | 0.092 |

Overall feed intake was slightly (but not significantly) higher for CH4 than for control. During week 3-5, for steers not receiving ionophore, CH4 had a significantly (P<0.05) higher intake than controls (10.56 vs 10.12), whilst no effect of CH4 was observed for animals receiving ionophore. Also during this period, for steers on the low-roughage diets, CH4 tended (P<0.15) to have higher intakes than controls (10.14 vs 9.80), whilst no effect of CH4 was observed for animals on the high-roughage diets.

TABLE 9

Average daily gain (kg per animal per day) for CH4-treatment vs control (no CH4 added), for various periods in the feedlot.

| Feedlot - period | Treatment | | P-value | s.e. |
|---|---|---|---|---|
| | Plus CH4 | Control (no CH4) | | |
| Week 1-2 | 1.76 | 1.81 | 0.51 | 0.053 |
| Week 3-5 | 2.09 | 1.97 | 0.04 | 0.040 |
| Week 1-13 | 2.19 | 2.20 | 0.67 | 0.019 |

Overall average daily gain (ADG) during the critical period of week 3-5 was significantly (P=0.04) higher for CH4 than control treatments. During week 1-2 for all animals that did not receive CH4, the low-roughage treatment had a significantly (P<0.05) lower ADG than the high-roughage treatment (1.61 vs 2.02). However, for animals that did receive CH4, ADG was not significantly lower on low-roughage as compared to high-roughage diets (1.70 vs 1.83). During week 3-5, for animals not receiving an ionophore, CH4 had a significantly (P<0.05) higher ADG than control animals (2.15 vs 1.96).

TABLE 10

Feed conversion ratio (kg feed per kg gain) for CH4-treatment vs control (no CH4 added), for various periods in the feedlot.

| Feedlot - period | Treatment | | P-value | s.e. |
|---|---|---|---|---|
| | Plus CH4 | Control (no CH4) | | |
| Week 1-2 | 4.25 | 4.12 | 0.43 | 0.111 |
| Week 3-5 | 4.89 | 5.14 | 0.04 | 0.081 |
| Week 1-13 | 5.06 | 5.02 | 0.35 | 0.027 |

Overall animals treated with CH4 had a significant (P=0.04) ca 5% improvement in feed conversion ratio (FCR) over control animals during week 3-5. During week 1-2 for all animals that did not receive CH4, the low-roughage treatment had a significantly (P=0.06) higher (less desireable) FCR than the high-roughage treatment (4.42 vs 3.83). However, for animals that did receive CH4, FCR was not significantly higher (less desireable) on low-roughage as compared to high-roughage diets (4.24 vs 4.25).

TABLE 11

Number of times (including multiple pulls of the same animal) and number of animals (multiple pulls of the same animal count only as one) that animals were pulled and treated for acidosis and bloat.

| | | Treatment | | |
|---|---|---|---|---|
| | | +CH4 | Contrl (−CH4) | TOTAL: |
| Total number of pulls (incidents) | Roughage - Low | 6 | 21 | 27 |
| | Roughage - Hi | 6 | 4 | 10 |
| | TOTAL: | 12 | 25 | 37 |
| Total number of pulls (incidents) | Roughage - Low | 4 | 15 | 19 |
| | Roughage - Hi | 5 | 2 | 7 |
| | TOTAL: | 9 | 17 | 26 |

For the CH4 treatments only half the number of animals suffered from acidosis symptoms (one or more times) as compared to the controls. The same trend was observed if the total numbers of acidosis incidents was considered. It is also clear that acidosis was much more prevalent on the low-roughage diet and that CH4 treatment alleviated the problem on the low-roughage diet.

Identification of Isolates using Phylogenetics, Based on 16S rRNA Gene Sequences.

Comparative sequencing results showed that our isolates, which are representatives of a larger phenotypically homogenous group, are between 97 and 99% similar (Table 12). Table 13 outlines positions of signature nucleotides suitable to distinguish the two recent *Megasphaera elsdenii* isolates and the ATCC strains from each other. Insertions and deletions accounted for 22% of nucleotide differences between the four strains. The major nucleotide sequence differences between the strains occur at nucleotide positions 529-536 and 1105-1120 (Table 13). The high sequence similarity displayed between the different *M. elsdenii* strains is also consistent with their similar phenotypic characteristics (Wiederhold, 1994), which is furthermore reflected by their tight phylogenetic clustering. Strains of the species *M. elsdenii* share only 91 to 92% sequence similarity with *M. cerevisiae*, and the two species form distinct clusters in the phylogenetic tree. The *M. elsdenii* cluster bifurcates into two monophyletic groups that evolved from the same ancestral taxonomic unit (ATU). The ATU from which *M. cerevisiae* evolved, however, predates the one from which the *M. elsdenii* cluster evolved. The short branch lengths between *M. elsdenii* strains (OTU's) and their respective ATU's also indicate that they have evolved more recently than the more deeply branched *M. cerevisiae*.

TABLE 12

Sequence similarity matrix of 16S rDNA sequences of *M. elsdenii* and *M. cerevisiae*.

| | ATCC 17752 | ATCC 25940 | CH7 | CH4 | % G + C |
|---|---|---|---|---|---|
| *M. cerevisiae* | 92.0 | 92.0 | 91.5 | 91.5 | 54.3 |
| ATCC 25940 | 99.0 | | 98.5 | 98.1 | 54.4 |
| CH4 | 98.2 | 98.1 | 99.0 | | 54.9 |
| CH7 | 97.7 | | | | 54.8 |
| ATCC 17752 | | | | | 53.1 |

Sequence similarity values are based on a comparison of a total of 1388 unambiguously aligned nucleotide positions. The % G + C refer only to the respective aligned 16S rDNA sequences.

TABLE 13

Sequence signatures defining different *M. elsdenii* isolates and strains

| | | Nucleotides | | |
|---|---|---|---|---|
| Position [a] | ATCC 25940 [b] | CH4 | CH7 | ATCC 17752 |
| 87 | G | G | A | G |
| 105 | C | T | C | T |
| 170 | T | C | C | T |
| 221 | T | C | C | T |
| 241 | G | A | A | G |
| 283 | A | G | G | A |
| 418 | A | * | * | * |
| 529-530 | CG | * | * | CG |
| 533-536 | CG ** | CGAC | CGAC | GC ** |
| 539 | T | C | C | T |
| 550-552 | TAC | CGT | CGT | TAT |
| 556 | G | A | A | G |
| 711 | G | G | G | C |
| 718 | * | * | * | G |
| 850 | A | A | G | A |
| 1084 | A | G | A | A |
| 1105-1108 | TGGA | AGGG | AGGG | TGGA |

TABLE 13-continued

Sequence signatures defining different
M. elsdenii isolates and strains

| Position[a] | ATCC 25940[b] | Nucleotides | | |
|---|---|---|---|---|
| | | CH4 | CH7 | ATCC 17752 |
| 1117-1120 | TCCA | CCCT | CCCT | TCCA |
| 1290 | A | * | A | * |
| 1297-1300 | AAGT | CGGC | AAGT | CGGC |
| 1396 | A | C | A | A |
| 1425 | A | A | G | A |
| 1437 | G | A | C | G |
| 1492 | T | C | C | T |

[a] E. coli numbering system (Brosius et al., 1978).
[b] denotes the type strain.
An asterisk indicates where a gap was introduced during the alignment as a result of the occurrence of a nucleotide deletion or insertion at any one position of the sequences of the respective isolates and strains.

Figure 3:
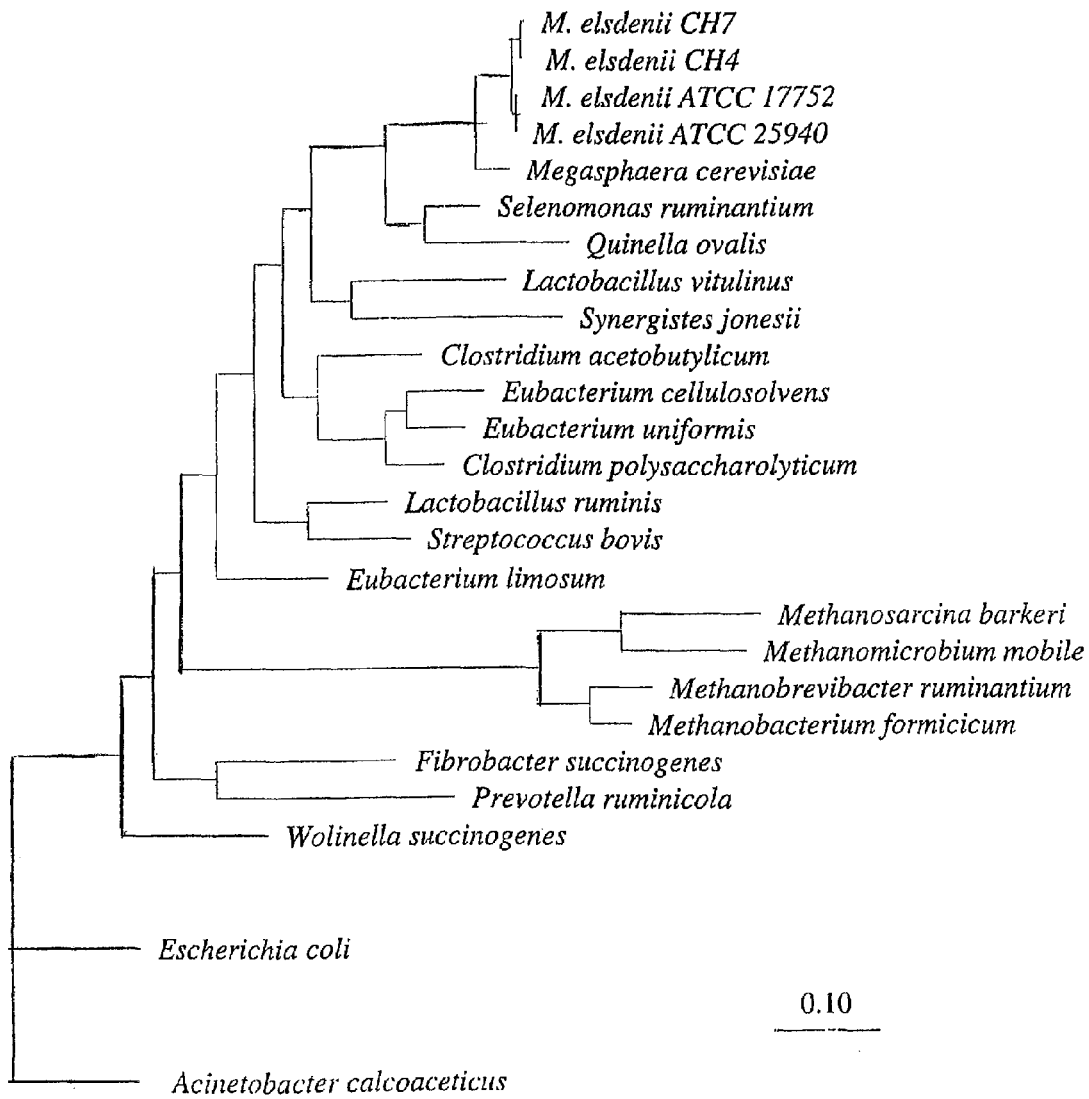
FIG. 3 is the phylogenetic tree of *M. elsdenii* according to the present invention.

The maximum likelihood method, which involves finding a tree, which gives the highest probability of giving rise to the observed sequence data (Felsenstein, 1981), was used to infer a phylogenetic tree from the sequences included in the alignment profile (FIG. 3). This method has the advantage above traditional parsimony methods, which could lead to inference of erroneous trees if different lineages evolve at unequal rates, in that it allows for evolutionary rates to differ between different lineages (Felsenstein, 1981). Since tree topology is also affected by the number of organisms used and the selection of the outgroups (Stackebrandt and Ludwig, 1994; Stackebrandt and Rainey, 1995), a number of apparently related and apparently unrelated organisms, occurring in the rumen was included in an alignment profile. This was subsequently used to construct the tree. Although the phylogenetic tree was inferred from only nearly complete (92%) 16S rRNA gene sequences, which could reduce resolution between very closely related organisms (Utaker et al., 1995; Li and Graur, 1991), the general topology of trees derived from either complete or partial sequences has been shown to be in overall agreement with each other (Van Camp et al., 1993, Vandamme et al., 1996).

Vandamme et al. (1996) proposed that different isolates should be regarded members of the same species if they share more than 97% rRNA sequence homology, show phenotypic consistency and exhibit a significant degree of DNA: DNA hybridization. Although the relationship between DNA similarity and 16S rRNA sequence homology between organisms is anything but linear, Fox et al. (1992) proposed that effective 16S rRNA sequence identity should imply that two organisms are members of the same species, since it would almost certainly be validated by the DNA: DNA hybridization. Although 16S rRNA sequence data alone may not be sufficient in all cases to define a species, it is extremely useful in determining to which species a strain probably belongs, once the relevant species is represented in a 16S rRNA sequence data base. Strains with almost identical 16S rRNA sequences should be assigned to the same "rRNA superspecies" or "rRNA species complex". It would thus be appropriate to assign isolates CH4 and CH7, phenotypically presumptively identified M. elsdenii strains, to the same rRNA species complex, which would include reference strains ATCC 25940, the type strain of the species, and ATCC 17752. Since the phylogenetic relationships of the respective isolates are furthermore consistent with their phenotypic characteristics, these isolates can be considered strains of the species Megasphaera elsdenii. The fact that M. cerevisiae and M. elsdenii share only 92% 16S rDNA sequence homology, confirms, together with genotypic and phenotypic data, the division of the genus into two well resolved species.

Of the rumen bacteria included in this study the ones which appear to be most closely related to the Megasphaera cluster are Selenomonas ruminantium and Quinella ovalis. The apparent phylogenetic relationship between Megasphaera elsdenii and Selenomonas ruminantium is consistent with some phenotypic and genotypic characteristics which the two species share, such as similar DNA G+C content (53-54%), anaerobic nature, chemoorganotrophic metabolism and utilization of a similar range of substrates (Stackebrandt et al., 1985; Stewart and Bryant, 1988; Haikara, 1992). The work of Stackebrandt et al. (1985), who made use of the oligonucleotide cataloguing technique for phylogenetic inference between the species, supports this phylogenetic relationship. Selenomonas ruminantium on the other hand is also closely related to the relatively unknown Quinella ovalis, an organism that proliferates in the rumen when sugar rich diets are fed to the animal. These organisms, although not established in culture yet, share some physiological characteristics with the large selenomonads found in sheep (Stewart and Bryant, 1988). As expected, the most distant relatives of Megasphaera that occur in the rumen are those contained in the archaeal methanogen cluster, the members of which are believed to have appeared approximately 600 to 800 million years ago (van Soest, 1994; Woese, 1987). The evolutionary rates of these organisms are also slower than that of the Bacteria, and the primitiveness of the group is clearly reflected by the deeply branched methanogen cluster.

The recent divergence of the different M. elsdenii strains could possibly be attributed to a refinement of its phenotype in order to adapt to the highly selective conditions in the rumen. According to Woese (1987), the evolution of the phenotype of an organism is a process during which new or more efficient traits are gained in order to survive in its particular niche. Refinement would result in the organisms being metabolically versatile, as is the case with Megasphaera. The slower evolving methanogens on the other hand are metabolically monotonous by comparison.

This study has demonstrated the suitability of 16S rDNA sequencing to distinguish between closely related strains of the species M. elsdenii. Furthermore, it provided a phylogenetic framework for identification of recently isolated strains that have been characterized phenotypically. The framework would be of particular value in serving as a basis for the design of species and strain-specific probes intended for rumen ecological studies.

CONCLUSIONS

Isolation

The incorporation of bromocresol purple to IRFL medium to facilitate detection of lactate-utilizing bacteria proved to be successful in the case of the faster-growing lactate-utilizes, which were of prime interest in this study. In the early stages of incubation these produced purple zones, concentric with the colonies, which contrasted clearly with the yellowish background of the agar medium. However, on extended incubation the pH gradient surrounding the colonies dissipated due to diffusion of ions and the whole background became purple. Differentiation between colonies of slower-growing lactate-utilizes and those of organisms growing on other carbon sources present in the rumen fluid supplement then became difficult. M. elsdenii is not the dominant lactate-utilizing species in animals on high-concentrate diets (Mackie et al., 1978; Mackie & Gilchrist, 1979; Mackie et al., 1984; van Gylswyk, 1990), but there are a number of reasons why they may have predominated in the selection and screening procedures.

Some of the colonies screened consisted of Selenomonads and other morphological types. Most of these colonies were not chosen as there was not a positive indication that lactate could be utilized in the presence of soluble sugars. Russell & Baldwin (1978) showed that *M. elsdenii* B159 used glucose, maltose and lactate, but not sucrose simultaneously in a multi-substrate medium. Marounek et al. (1989) showed that for four strains of *M. elsdenii* lactate was used more rapidly than glucose in media with both carbon sources.

Certain other laboratories, which have studied the possibility of inoculating ruminants on high-concentrate diets with lactate-utilizing organisms to prevent an accumulation of lactate, have also worked with *M. elsdenii* strains (Das, 1979; Leedle et al., 1991; Robinson et al., 1992; Kung & Hession, 1995; Wiryawan & Brooker, 1995). It was not possible to compare the growth rates of the AW and CH isolates to strains in the literature to determine if they had faster growth rates and if they were more acid tolerant, as no results were available in literature. The AW and CH isolates can however be compared to the type strain, *M. elsdenii* ATCC 25940.

For the AW isolates the range of pH values at which growth was determined was not sufficient to determine the pH range for the isolates or the optimum pH for growth. However, it can be assumed that the optimum would be above pH 5.7 and the lowest pH would lie between pH 4.5 and pH 4.9 for all but four of the isolates, as there was no growth on IRFL plates at pH 4.5. This agrees with work done on the type strain of *M. elsdenii* ATCC 25940. The pH range for the type strain of *M. elsdenii* ATCC 25940 is pH 4.6 to 7.8 with the optimum for growth at pH 6.05 (Therion et al., 1982).

For the CH isolates the optimum pH for growth is between pH 5 and 6. In the range of pH values tested, the highest growth rates were found at pH 5.5. Both sets of isolates had higher growth rates on SDL medium than the type strain. The growth rates obtained for *M. elsdenii* ATCC 25940 in SDL medium is comparable to that obtained by earlier workers on lactate medium (Therion et al., 1982).

The growth rates of the isolates on lactate were higher than on glucose and maltose. This is in agreement with a previous study on *M. elsdenii* ATCC 25940, where growth rates on lactate medium between pH 5.0 and pH 6.5 was found to be higher than in glucose medium (Therion et al., 1982). Outside this pH range growth rates on glucose were higher. A study on substrate preference in rumen bacteria reported that growth of *M. elsdenii* B159 on lactate was slower than on glucose and maltose, however the pH of the media in the study was above pH 6.5, being between 6.75 and 6.9 (Russell & Baldwin, 1978).

The composition of fermentation end products on lactate medium has been determined for four strains of *M. elsdenii*, including the type strain LC1 or ATCC 25940 (Marounek et al, 1989). These results showed strain-to-strain variability in the proportions of fatty acids formed. Three of the strains produced little or no valeric acid while 22 mol % of the end-products of *M. elsdenii* L8 was valeric acid (Marounek et al., 1989). The nine AW isolates tested in the present study did not exhibit as much strain-to-strain variability as was the case in the strains tested by Marounek et al. (1989), but are similar to *M. elsdenii* L8, which was isolated from the rumen of a calf on a milk diet, as valeric acid was produced. CH4, however, produced the same fermentation end-products as the type strain.

From the point of view of maximum biomass output rate in SDL medium strain AW15 would be the organism of choice for larger scale production of cells for animal experiments with CH4 and AW01 being next in line. The time required to produce 100 g dry mass of cells on SDL medium in a chemostat of 51 working volume would be 1.9 days for AW15 and 2.1 days for CH4 and AW01.

The growth rates of the selected isolates on lactate are high compared to the type strain of *M. elsdenii*. The isolates are acid tolerant and can grow at pH values below 5.0. They are resistant to ionophores, commonly added to feedlot diets, and can utilize both isomers of lactic acid even in the presence of glucose and maltose. The fermentation end products from lactate are VFA, which are an important energy source for the ruminant. Propionate production is especially important in the feedlot industry, as propionate is the main source of glucose for the ruminant tissues. The isolates, therefore, have the characteristics required for an effective product to combat lactic acidosis in ruminants.

Cultivation of the lactate utilizes was successful using a medium that did not contain any rumen fluid. The only modification to the original medium was the increase in the vitamin content and the addition of yeast extract to the medium. Bacteria survived remarkably well on this medium at 4° C. for up to 20 days, when used as working cultures.

The technique of using a pH-auxostat for the enrichment of lactate-utilizing rumen bacteria, with a predetermined combination of biochemical/physiological attributes, which would make them potentially highly suitable for preventing and combating lactic acidosis in feedlot animals was very successful. In most cases a fast-growing, morphologically homogeneous population became established in the fermenter within two days after the start of a run. Subsequent tests on the cultures that were isolated from the fermenter contents by plating, confirmed that the cultures possessed the desired combination of characteristics.

Presumptive identification of the isolates from the enrichments showed that all but one belonged to the species *Megasphaera elsdenii*.

TABLE 14

A comparison between the pH-auxostat isolation technique and a conventional spread plate screening technique.

| Parameter | Conventional spread plate | Auxostat |
|---|---|---|
| Time elapsed (days) | 90 | 9 |
| Man hours spent | 180 | 7 |
| Sample: bacterial load (cfu) | $12 \times 10^{10}$ | $14 \times 10^{12}$ |
| Maximum specific growth rate ($h^{-1}$) | 0.91 | 0.90 |
| Biomass yield ($g \cdot l^{-1}$) | 0.60 | 0.59 |
| Biomass output rate $g(l \cdot h)^{-1}$ | 0.39 | 0.39 |

Since the isolates performed better than ATCC 25940 at pH values below 6.0, they would be more suited to the ruminal pH encountered by feedlot animals that usually is below pH 6.0. Furthermore, CH4 proved to be the best suited isolate for trial experimentation on feedlot animals.

Cultivation of the lactate utilizing isolates on glucose proved not to be a proposition due to the slow growth rates obtained compared to the growth rates obtained on lactate.

The thirty cows that were dosed with organism CH4 produced significantly more milk (P=0.10), had a higher average body weight (P=0.02) and body condition score (P=0.06). The milk fat percentage of cows receiving the 60% concentrate diet +CH4 were also significantly increased (3.57% vs. 3.23%).

Dairy Animal Trials

Dry matter intakes did not differ but milk production was significantly increased by 3.4 kg/d from 35.9 to 39.3 kg/d (P=0.06) when cows were fed the 70% concentrate diet and were dosed with organism CH4. Milk production tended to be increased (P=0.13) when all dosed cows were compared to all non-dosed cows. Body weight and condition score were increased (P=0.02) when high producing cows receiving the high concentrate diet were dosed with organism CH4. The dosing of cows receiving the 60% concentrate diet resulted in a significant increase in milk fat percentage (P=0.06) with a tendency towards increased milk protein (P=0.11). Milk components play an important role in current milk payment schemes.

Dosing cows with organism CH4 significantly increased milk production and positively affected milk composition, body weight and body condition score. Dry matter intakes were not affected; therefore results suggest that dosing of cows with organism CH4 caused a more favorable rumen environment, which resulted in improved utilization of nutrients.

Feedlot Animal Trials

The significant improvement in average daily gain (ADG) and feed conversion ratio (FCR) during the critical period in the feedlot (week 3-5), as well as the overall decrease in digestive disturbances, for CH4-treated animals as compared to controls, show that treatment of feedlot animals with CH4 can be effective in the following ways:

It aided the adaptation from roughage to concentrate diets, as inherent in this experiment. CH4 also alleviated the poorer performance of the low-roughage diet as compared to the high-roughage diet during the early adaptation stages.

The application method used here for CH4 was effective in allowing its expression as intended.

The use of CH4 was effective in preventing acidosis, as evidenced directly by less observed cases of acidosis and indirectly by improved performance during the critical feedlot phase when acidosis is most likely to occur. All this was observed on diets and dietary regimes with an exceptionally high risk of acidosis (especially in the early feedlot stages), and was more pronounced where no ionophore was used.

CH4 may be used as a veterinary agent to help in the prevention and/or treatment of acidosis, as evidenced by the sharp decline in acidosis cases for CH4 as compared to controls.

CH4 may be used to improve feedlot performance including growth rate (and by implication to decrease time required for finishing) and feed conversion efficiency.

CH4 can be used to allow the feeding of higher-concentrate diets, i.e. the use of less roughage, and to increase the rate of change from high roughage to high concentrate diets, i.e. also the use of less roughage. This is further supported by the observations, during the early feedlot phases, that the negative effect of low-roughage diets, as compared to the high-roughage diets, was largely alleviated when CH4 was added.

The applicants have further found that, in comparison with the known strains of *M. elsdenii*, the *M. elsdenii* CH4 strain is:

highly active and adapted to proliferate in the rumen of animals on high-concentrate diets;

capable of proliferating at relatively low pH values below pH 5.0 and as low as 4.5, characterized as acute acidosis;

resistant to ionophore antibiotics commonly added to feedlot diets; and capable of preferentially using lactate as a carbon source even in the presence of soluble carbohydrates such as glucose and maltose.

Further advantages of this strain are that it:

has a relatively high growth rate, i.e. more than $0.938\ h^{-1}$;

has the ability to grow on reducing sugars as well as on lactate;

has a relatively high biomass output rate, i.e. more than $0.39\ g\ (l.h)^{-1}$;

is ionophore resistant;

produces predominantly acetate and not predominantly propionate and butyrate; and has a unique 16S rRNA sequence and is therefore a new strain.

The applicants have yet further found that animals challenged with maltose, fed directly into the rumen, or abruptly changed from a roughage to a high-concentrate diet, produced no measurable build-up of lactate in the rumen when inoculated with CH4.

Furthermore, high producing dairy cows inoculated with CH4 has a 2.4 to 3.2 liters higher production of milk, than control animals not inoculated with CH4. The body condition score as well as body weight of the inoculated cows were statistically significantly higher than the control animals.

It will be appreciated that variations in detail are possible with a microorganism according to the invention and its uses without departing from the scope of the appended claims.

REFERENCES

1. Abdo, K. M. & Cahilly, G. M. (1974). Ruminant feed additive and method of preparing the same. U.S. Pat. No. 3,857,971, 1-30.
2. Allison, M. J., Bucklin, J. A. & Dougherty, R. W. (1964). Ruminal changes after overfeeding with wheat and the effect of intraruminal inoculation on adaptation to a ration containing wheat. *J Anim Sci* 23, 1164-1170.
3. Braun, U., Rihs, T. & Schefer, U. (1992). Ruminal lactic acidosis in sheep and goats. *Veterinary Record* 130, 343-349.
4. Das, N. K. (1979). Ruminant feed additive. U.S. Pat. No. 4,138,498, 1-14.
5. Dawson, K. A. & Allison, M. J. (1988). Digestive disorders and nutritional toxicity. In The rumen microbial ecosystem, pp. 445-459. Edited by P. N. Hobson. London: Elsevier Applied Science.
6. Gray, W. M. (1978). Microbial interactions in defined continuous culture systems effecting anaerobic cellulose degradation, PhD thesis: Clemson University.
7. Hession, A. O. & Kung, L., Jr. (1992). Altering rumen fermentation by microbial inoculation with lactate-utilizing microorganisms. *J Anim Sci* 70, 311. (Abstract)
8. Jannasch, H. W., 1977. Growth kinetics of aquatic bacteria. In: *Aquatic Microbiology*. Skinner, F. A. & Shewan, J. M. (Eds), Academic Press, London, 55-57.
9. Kung, L., Jr. & Hession, A. O. (1995). Preventing in vitro lactate accumulation in ruminal fermentations by inoculation with *Megasphaera elsdenii*. *J Anim Sci* 73, 250-256.
10. Krieg, R., 1981. Enrichment and isolation. In: *Manual of Methods for General Bacteriology*. Gerhardt, P. (Ed.), American Society for Microbiology, Washington, 112-114.
11. Lederberg, J. & Lederberg, E. M. (1952). Replica plating and indirect selection of bacterial mutants, *J Bact* 63, 399-406.

12. Leedle, J. A. Z., Greening, R. C. & Smolenski, W. J. (1991). Ruminal bacterium for preventing lactic acidosis. International Application No : PCT/US91/00857 1-41.
13. Mackie, R. I., Gilchrist F. M. C., Robberts, A. M., Hannah, P. E. & Schwartz, H. M. (1978). Microbiological and chemical changes in the rumen during the stepwise adaptation of sheep to high concentrate diets. *J agric Sci, Camb* 90, 241-242.
14. Mackie, R. I., Gilchrist, F. M. C. & Heath, S. (1984). An in vivo study of ruminal micro-organisms influencing lactate turnover and its contribution to volatile fatty acid production. *J agric Sci, Camb* 103, 37-51.
15. Mackie, R. I. & Gilchrist, F. M. C. (1979). Changes in lactate-producing and lactate-utilizing bacteria in relation to pH in the rumen of sheep during stepwise adaptation to a high-concentrate diet *Appl Environ Microbiol* 38, 422-430.
16. Mackie, R. I. & Heath. S. (1979). Enumeration and isolation of lactate-utilizing bacteria from the rumen of sheep. *Appl Environ Microbiol* 38, 416-421.
17. Marounek, M., Fliegrova, K. & Bartos, S. (1989). Metabolism and some characteristics of ruminal strains of *Megasphaera elsdenii*. *Appl Environ Microbiol* 55, 1570-1573.
18. Olumeyan, D. B., Nagaraja, T. G., Miller, G. W., Frey, R. A. & Boyer, J. E. (1986). Rumen microbial changes in cattle fed diets with or without salinomycin. *Appl Environ Microbiol* 51, 340-345.
19. PIRT, S. J., 1975. Principles of Microbe and Cell Cultivation. Blackwell Scientific Publications, Oxford, 41-210.
20. Pryce, (1969). A modification of the Barker-Summerson method for the determination of lactic acid. Analyst 94, 1151.
21. Robinson, J. A., Smolenski, W. J., Greening, R. C., Ogilvie, M. L., Bell, R. L., Barsuhn, K. & Peters, J. P. (1992). Prevention of acute acidosis and enhancement of feed intake in the bovine by *Megasphaera elsdenii* 407A *J Anim Sci* 70, 310. (Abstract)
22. Rogosa, M. (1984). Anaerobic Gram-negative cocci. In Bergey's manual of systematic bacteriology Volume 1, pp. 680-685. Edited by N. R. Krieg & J. G. Holt, Baltimore/London: Williams & Wilkins.
23. Russell, J. B. & Baldwin, R. L. (1978). Substrate preferences in rumen bacteria: evidence of catabolite regulatory mechanisms. *Appl Environ Microbiol* 36, 319-329.
24. Slyter, L. L. (1976). Influence of acidosis on rumen function. *J Anim Sci* 43, 910-929.
25. Stewart, C. S. & Bryant, M. P. (1988). The rumen bacteria. In The rumen microbial ecosystem, pp. 21-75. Edited by P. N. Hobson. London: Elsevier Applied Science.
26. Therion, J. J., Kistner, A & Kornelius, J. H. (1982). Effect of pH on growth rates of rumen amylolytic and lactilytic bacteria. *Appl Environ Microbiol* 44, 428-434.
27. Van Gylswyk, N. O. (1990). Enumeration and presumptive identification of some functional groups of bacteria in the rumen of dairy cows fed grass silage-based diets. *FEMS Microbiol Ecol* 73, 243-254.
28. Veldkamp, H. 1970. Enrichment cultures of prokaryotic organisms. In: *Methods in Microbiology*, Vol. 3A, Norris, J. R. & Ribbons, D. W. (Eds), Academic Press, London, 305-361.
29. Wilker, B. L., Paege, L. M. & Baker, E. (1971). Bacterial culture for facilitating dietary adaptation of ruminants. Patent Office, London 1251483, 1-13.
30. Wiryawan, K G. & Brooker, J. D. (1995). Probiotic control of lactate accumulation in acutely grained sheep. *Aust J Agric Res* 46, 1555-1568.

Cow Experiments
31. DAWSON, J. A. 1995. The use of yeast strain 8417 in manipulating ruminant high concentrate diets. Proc. 56th Minnesota Nutr. Conf. & Alltech Inc. Technical Symposium. Sep. 18-20, Bloomington, Minn.
32. DONOVAN, J. 1997. Subacute acidosis is costing no millions. Hoards Dairyman, Sep. 25 p. 666.
33. HALL, M. B. 1999. Management strategies against ruminal acidosis. Proc. Florida Ruminant Nutr. Symp. Univ. Florida, Gainesville, Fla.
34. HUTJENS, M. F. 1995. Feeding applications for the high producing cow. Cornell Nutr. Conf. Oct. 24-26. Dept Anim. Sci., Cornell Univ., Ithaca, N.Y.
35. HUTJENS, M. F. 1999. How and when feed additives may or may not pay, Hoards, Dairy man, Sep. 25, 1999.
36. KELLY, E. R. & LEAVER, J. D. 1990. Lameness in dairy cattle and the type of concentrates given. *Anim. Prod.* 51: 221.
37. KUNG, L. 2000. Direct fed microbials for dairy cows. Proc. Florida Ruminant Nutr. Symp. Univ. Florida, Gainesville, Fla.
38. KUNG, L & HESSION, O. A. 1995. Altering rumen fermentation by microbial inoculation with lactate utilizing micro-organisms. *J. Anim. Sci.* 73:250.
39. MANSON, R. J. & LEAVER, J. D. 1988. The influence of concentrate amount on locomotion and clinical lameness in dairy cattle. *Anim. Prod.* 47-185.
40. McDANIEL, B. T. & WILK, J. C. 1989. Lameness in dairy cattle. Proc. Southwest Nutr. Mgmt, Conf., Feb. 2-3, Dept Anim. Sci., Univ. Arizona, Tucson, Ariz.
41. NOCEK, J. E. 1995. Energy metabolism and rumen acidosis. Proc. Tri-state Dairy Nutr. Conf., May 23-24. Indiana Univ., Fort Wayne, Ind.
42. NOCEK, H. E. 1997. Bovine acidosis. Implications on laminitis. *J. Dairy Sci* 80:1005.
43. NORDLUND, K. V. 1995. Questions and answers regarding rumenocentesis and the diagnosis of herd based subacute rumen acidosis. Proc. 4-State Applied Nutr. Conf., Aug. 2-3, Univ. Wisconsin, Extension, Madison, Wis.
44. NORDLUND, K. V., GARRET, E. F. & OETZEL, G. R. 1995. Herd based rumenocentesis: A clinical approach to the diagnosis of subacute rumen acidosis. The Compendium Food Animal, Aug. 1995, p. 48.
45. OETZEL, G. R. & SMITH, R. A. 2000. Clinical aspects of ruminal acidosis in dairy cattle. Proc. $33^{rd}$. Conf. American Assoc. Bov. Pract, Rapid City, S.D. Sep. 21-23.
46. OWENS, F. N., SECRIST, D., HILL, J. & GILL, D. 1996. A new look at acidosis. Proc. Southwest Nutr. Conf., Feb. 1, Phoenix, Ariz.
47, VOGEL, G. J. & PARROT, C. 1994. Mortality survey in feedyards: The incidence of death from digestive, respiratory and other causes in feedyards on the great plains. The Compendium Feb. 1994: Food Animal, p. 227.
48. ROBINSON, J. A., SMOLENSKI, W. J., GREENING, R. C., OGILVIE, R. L., BELL, R. L., BARSUHN, K & PETERS, J. P. 1992 Prevention of acute acidosis and enhancement of feed intake in the bovine by *Megasphaera elsdenii* 407A. *J. Anim Sci*. (Suppl. 1): 310 (Abstr)

Phylogenetics
49. Ausubel, F. M., R. Brent, R. E. Kingston, D. D. Moore, J. A. Smith, J. G. Seidman, and K. Struhl. 1987. Current Protocols in Molecular Biology. Vol 1 and 2. John Wiley and Sons, New York,
50. Brosius, J., M. L. Palmer, P. J. Kennedy and H. F. Noller. 1978. Complete nucleotide sequence of the 16S ribosomal RNA gene from *E. coli*. Proc. Natl. Acad. Sci. 75:4801-4805.

51. Dorsch, M. and E. Stackebrandt. 1992 Some modifications in the procedure of direct sequencing of PCR amplified 16S rDNA. J. Microbiol. Methods. 16:271-279.
52. Elsden, S. R. and D. Lewis. 1953. The production of fatty acids by a gram-negative coccus. Biochem. J. 55:183-189.
53. Elsden, S. R., B. E. Volcani, F. M. C. Gilchrist and D. Lewis. 1956. Properties of a fatty acid forming organism isolated from the rumen of sheep. J. Bacteriol. 72:681-689.
54. Engelmann, U. and N. Weis. 1985. *Megasphaera cerevisiae* sp. nov.: A new Gram-negative obligately anaerobic coccus isolated from spoiled beer. Syst Appl. Microbiol. 6:287-290.
55. Felsenstein, J. 1981. Evolutionary trees from DNA sequences: a maximum likelihood approach. J. Mol. Evol. 17:368-376.
56. Fox, G. E., J. D. Wisotzkey and P. Jurtshuk, Jr. 1992 How close is close: 16S rRNA sequence identity may not be sufficient to guarantee species identity. Int. J. Syst Bacteriol. 42:166-170.
57. *Genetics Computer Group. 1991. Program manual for the GCG package, version 7. Madison, Wis., USA
58. Gutierrez, J., R. E. Davis, I. L. Lindahl and E. J. Warwick. 1959. Bacterial changes in the rumen during the onset of feed-lot bloat of cattle and characteristics of *Peptostreptococcus elsdenii* n. sp, Appl. Microbiol. 7:16-22.
59. Haikara, A 1992. The genera *Pectinatus* and *Megasphaera*, p. 1993-2004. In A. Barlows, H. Trooper, M. Dworkin, W. Harder and K.-H. Schleifer (ed), The prokaryotes. A handbook on the biology of bacteria: ecophysiology, isolation, identification, application, 2nd ed., vol ψψ. Springer Verlag, New York.
60. Hutson, R. A., D. E. Thompson, and M. D. Collins. 1993. Generic interrelationships of saccharolytic *Clostidium botulinum* types B, E and F and related clostridia as revealed by small-subunit rRNA gene sequences. FEMS Microbiol. Lett. 108:103-110.
61. Lane, D. J., B. Pace, G. J. Olsen, D. A. Stahl, M. L. Sogin, and N. R. Pace. 1985. Rapid determination of 16S ribosomal RNA sequences for phylogenetic analyses. Proc. Natl. Acad. Sci. USA 82:6955-6959.
62. Li, W. -H., and D. Graur. 1991. Fundamentals of molecular evolution. Sunderland, Mass. Sinauer Associates Inc.
63. Maidak, B. L., Olsen, G. J., Larsen, N., Overbeek, R., McCaughey, M. J. and Woese, C. R. 1996. The ribosomal database project (RDP). *Nucleic Acids Res* 24:82-85.
64. Olsen, G. J., H. Matsuda, R. Hagstrom, and R. Overbeek. 1994. FastDNAml—a tool for construction of phylogenetic trees of DNA sequences using maximum likelihood. CABIOS 10:41-48.
65. Rogosa, M. 1971. Transfer of *Peptostreptococcus elsdenii* Gutierrez et al. to a new genus, *Megasphaera* [*M. elsdenii* (Gutierrez et al.) comb. nov]. Int. J. Syst Bacteriol. 21:187-189.
66. *Sambrook, J., Fritsch, E. F. and Maniatis, T. 1989. Molecular cloning. A laboratory manual. Second edition (Eds. Ford, N., Nolan, C. and Ferguson, M.). Cold Spring Harbor, Laboratory Press.
67. Smith, S. 1992 Genetic Data Environment, version 2.0: Documentation. Harvard University & University of Illinois.
68. Stackebrandt E., and W. Ludwig. 1994. The importance of choosing outgroup reference organisms in phylogenetic studies: the *Atopobium* case. Syst Appl. Microbiol. 17:39-43.
69. *Stackebrandt, E., and F. A. Rainey. 1995. Partial and complete 16S rDNA sequences, their use in generation of 16S rDNA phylogenetic trees and their implications in molecular ecological studies. Molecular Microbial Ecology Manual 3.1.1:1-17. Kuwer Academic Publishers, Netherlands.
70. Stackebrandt, E., H. Pohla, R. Kroppenstedt, H. Hippe, and C. R. Woese. 1985. 16S rRNA analyses of *Sporomusa, Selenomonas*, and *Megasphaera*: on the phylogenetic origin of Gram-positive Eubacteria. Arch. Microbiol. 143: 270-276.
71. Stackebrandt, E., and O. Charfreitag. 1990. Partial 16S rRNA primary structure of five *Actinomyces* species: phylogenetic implications and development of an *Actinomyces isrealii*-specific oligonucleotide probe. J. Gen. Microbiol. 136:37-43.
72. Stewart C. S., and M. P. Bryant 1988. The rumen bacteria. p. 21-75. In Hobson, P. N. (ed), The rumen microbial ecosystem., Elsevier Applied Science, London
73. Sugihara, P. T., V. L. Sutter, H. R., Attebery, K. S. Brichnell, and S. M. Finegold. 1974. Isolation of *Acidominococcus fermentans* and *Megasphaera elsdenii* from normal human feces. Appl. Microbiol. 27:274-275.
74. Utaker, J. B., L. Bakken, Q. Q. Jiang, and I. F. Nes. 1995. Phylogenetic analysis of seven new isolates of ammonia-oxidizing bacteria based on 16S rRNA gene sequences. Syst Appl. Microbiol. 18:549-559.
75. Van Camp, G., Y. Van De Peer, S. Nicolai, J.-M. Neefs, P. Vandamme, and R. De. Wachter. 1993. Structure of 16S and 23S ribosomal RNA genes in *Campylobacter* species: phylogenetic analysis of the genus *Campylobacter* and presence of internal transcribed spacers. Syst Appl. Microbiol. 16:361-368.
76. Vandamme, P., B. Pot M. Gillis, P. De Vos, K. Kersters, and J. Swings. 1996. Polyphasic taxonomy, a consensus approach to bacterial systematics. Microbiol. Rev. 60:407-438.
77. van Soest, P. J. 1994. Nutritional ecology of the ruminant $2^{nd}$ Edition. Comstock Publishing Associates, Ithaca.
78. Wiederhold, A. H. 1994. Isolation, selection and cultivation of lactic acid-utilizing rumen bacteria for the treatment of chronic and acute acidosis. MSc. thesis. University of Natal, Pietermaritzburg.
79. Woese, C. R. 1987. Bacterial evolution. Microbiol. Rev. 51:221-271.

The invention claimed is:

1. A biologically pure bacterial culture of an acid tolerant strain of *Megasphaera elsdenii* selected from the group consisting of the *M. elsdenii* strain CH3 deposited at NCIMB, Aberdeen, Scotland, UK under number NCIMB 41787, and the *M. elsdenii* strain CH7 deposited at NCIMB, Aberdeen, Scotland, UK under number NCIMB 41788, wherein the acid-tolerant strain has a maximum growth rate of at least about $0.5\,h^{-1}$ on lactate medium at pH 5.0.

2. The biologically pure bacterial culture of claim 1 which is further characterised by its ability to utilize lactate in the presence of a sugar selected from the group consisting of glucose and maltose.

3. A composition for facilitating the adaptation of ruminants from a roughage-based diet to a high-energy concentrate-based diet, the composition comprising the bacterial culture of claim 1.

4. A method for facilitating the adaptation of ruminants from a roughage-based diet to a high-energy concentrate-based diet, the method comprising administering to the rumen of said ruminants an effective amount of the composition of claim 3.

5. A feed-additive for ruminants comprising a carrier and an effective amount of the bacterial culture of claim 1.

6. The feed-additive according to claim 5 wherein the culture is disposed in an anaerobic container.

7. A method for the treatment of ruminal lactic acidosis comprising anaerobically administering to the rumen of a ruminant an effective amount of a bacterial culture according to claim 1.

8. The method of claim 7 wherein the method treats at least one ruininal lactic acidosis, rumenitis, ruminal lactic acidosis induced laminitis, ruminal lactic acidosis induced bloat and liver abscesses.

9. A composition for the treatment of ruminal lactic acidosis comprising an effective amount of a bacterial culture according to claim 1.

10. The composition of claim 9, wherein the method treats at least one of ruminal lactic acidosis, rumenitis, ruminal lactic acidosis induced laminitis, ruminal lactic acidosis induced bloat and liver abscesses in ruminants.

11. A preparation for the treatment of ruminal lactic acidosis comprising an inoculum of a bacterial culture according to claim 1 and a sterile anaerobic growth medium.

12. The preparation of claim 11 wherein the culture and the medium are disposed in separate chambers of an anaerobic container, wherein the chambers are anaerobically connectable to each other.

13. The preparation of claim 12, wherein the preparation treats at least one of ruminal lactic acidosis, rumenitis, ruminal lactic acidosis induced laminitis, ruminal acidosis induced bloat and liver abscesses in ruminants.

14. A method of achieving in a ruminant at least one of increased milk production; improved growth rate; lower incidence of lactic acidosis and related diseases; in feeds; and, the method comprising administering to the rumen of a ruminant an effective amount of the bacterial culture of claim 1.

15. A method according to claim 14 wherein the culture is administered anaerobically.

16. The biologically pure bacterial culture of claim 1, which is further characterised by its resistance to ionophores.

17. The biologically pure bacterial culture of claim 1, which is further characterised by its capability to produce predominantly acetate.

18. The biologically pure bacterial culture of claim 1 further characterised by a maximum growth rate of at least about 0.36 $h^{-1}$ on lactate medium at about pH 4.75.

19. The biologically pure bacterial culture of claim 1 wherein the acid-tolerant strain of *M elsdeni* has the identifying characteristics of a growth rate on lactate medium at pH 4.5 of at least 0.1 $h^{-1}$ and a maximum growth on lactate medium at pH 5.5 of at least about 0.86 $h^{-1}$.

* * * * *

SEQUENCE LISTING

<160> NUMBER OF SEQ ID NOS: 10

<210> SEQ ID NO 1
<211> LENGTH: 17
<212> TYPE: DNA
<213> ORGANISM: Artificial Sequence
<220> FEATURE:
<223> OTHER INFORMATION: Primers used to amplify and sequence the 16S -continued rRNA gene.

<400> SEQUENCE: 1
cggtgtgtac aaggccc                                                17

<210> SEQ ID NO 2
<211> LENGTH: 19
<212> TYPE: DNA
<213> ORGANISM: Artificial Sequence
<220> FEATURE:
<223> OTHER INFORMATION: Primers used to amplify and sequence the 16S
      rRNA gene.

<400> SEQUENCE: 2
cgtcatcccc gccttcctc                                              19

<210> SEQ ID NO 3
<211> LENGTH: 17
<212> TYPE: DNA
<213> ORGANISM: Artificial Sequence
<220> FEATURE:
<223> OTHER INFORMATION: Primers used to amplify and sequence the 16S
      rRNA gene.

<400> SEQUENCE: 3
cgattactag cgattcc                                                17

<210> SEQ ID NO 4
<211> LENGTH: 15
<212> TYPE: DNA
<213> ORGANISM: Artificial Sequence
<220> FEATURE:
<223> OTHER INFORMATION: Primers used to amplify and sequence the 16S
      rRNA gene.

<400> SEQUENCE: 4
tcgaattaaa ccaca                                                  15

<210> SEQ ID NO 5
<211> LENGTH: 17
<212> TYPE: DNA
<213> ORGANISM: Artificial Sequence
<220> FEATURE:
<223> OTHER INFORMATION: Primers used to amplify and sequence the 16S
      rRNA gene.

<400> SEQUENCE: 5
ctaccagggt atctaat                                                17

<210> SEQ ID NO 6
<211> LENGTH: 17
<212> TYPE: DNA
<213> ORGANISM: Artificial Sequence
<220> FEATURE:
<223> OTHER INFORMATION: Primers used to amplify and sequence the 16S
      rRNA gene.

<400> SEQUENCE: 6
ctgctgcctc ccgtagg                                                17

<210> SEQ ID NO 7
<211> LENGTH: 19
<212> TYPE: DNA
<213> ORGANISM: Artificial Sequence
<220> FEATURE:
<223> OTHER INFORMATION: Primers used to amplify and sequence the 16S
      rRNA gene.

```
<400> SEQUENCE: 7
agagtttgat cctggctca                                                      19

<210> SEQ ID NO 8
<211> LENGTH: 17
<212> TYPE: DNA
<213> ORGANISM: Artificial Sequence
<220> FEATURE:
<223> OTHER INFORMATION: Primers used to amplify and sequence the 16S
      rRNA gene.

<400> SEQUENCE: 8
ggaatcgcta gtaatcg                                                        17

<210> SEQ ID NO 9
<211> LENGTH: 17
<212> TYPE: DNA
<213> ORGANISM: Artificial Sequence
<220> FEATURE:
<223> OTHER INFORMATION: Primers used to amplify and sequence the 16S
      rRNA gene.

<400> SEQUENCE: 9
cctacgggag gcagcag                                                        17

<210> SEQ ID NO 10
<211> LENGTH: 15
<212> TYPE: DNA
<213> ORGANISM: Artificial Sequence
<220> FEATURE:
<223> OTHER INFORMATION: Primers used to amplify and sequence the 16S
      rRNA gene.

<400> SEQUENCE: 10
tgtggtttaa ttcga                                                          15
```